United States Patent [19]

Won

[11] Patent Number: 5,145,675
[45] Date of Patent: Sep. 8, 1992

[54] TWO STEP METHOD FOR PREPARATION OF CONTROLLED RELEASE FORMULATIONS

[75] Inventor: Richard Won, Palo Alto, Calif.

[73] Assignee: Advanced Polymer Systems, Inc., Redwood City, Calif.

[21] Appl. No.: 644,869

[22] Filed: Jan. 23, 1991

Related U.S. Application Data

[60] Continuation of Ser. No. 334,051, Apr. 5, 1989, abandoned, which is a division of Ser. No. 91,641, Aug. 31, 1987, abandoned, which is a continuation-in-part of Ser. No. 810,478, Dec. 18, 1985, abandoned, and a continuation-in-part of Ser. No. 846,321, Mar. 31, 1986, abandoned, and a continuation-in-part of Ser. No. 896,956, Aug. 15, 1986, abandoned, and a continuation-in-part of Ser. No. 925,081, Oct. 30, 1986, abandoned, and a continuation-in-part of Ser. No. 925,082, Oct. 30, 1986, abandoned, and a continuation-in-part of Ser. No. 932,613, Nov. 11, 1986, abandoned, and a continuation-in-part of Ser. No. 933,243, Nov. 21, 1986, abandoned, and a continuation-in-part of Ser. No. 936,520, Dec. 1, 1986, abandoned, Division of Ser. No. 940,754, Dec. 10, 1986, abandoned.

[51] Int. Cl.$^5$ ............................................. C08J 9/28
[52] U.S. Cl. ........................... 424/78.31; 424/78.02; 424/78.08; 424/78.31; 424/484; 424/489; 424/501
[58] Field of Search ............... 424/78, 83, 484, 489, 424/501, 78.02, 78.08, 78.31, 78.33

[56] References Cited

U.S. PATENT DOCUMENTS

| | | | |
|---|---|---|---|
| 3,328,256 | 6/1967 | Gaunt | 424/501 |
| 3,531,463 | 9/1970 | Gustafson | |
| 3,758,686 | 9/1973 | Sieger et al. | |
| 3,872,023 | 3/1975 | Baum et al. | |
| 3,985,298 | 10/1976 | Nichols | |
| 4,049,604 | 9/1977 | Morehourse, Jr. et al. | |
| 4,154,917 | 5/1979 | Miyake et al. | 523/128 |
| 4,221,871 | 9/1980 | Meitzner et al. | |
| 4,224,415 | 9/1980 | Meitzner et al. | |
| 4,282,216 | 8/1981 | Rovee et al. | |
| 4,321,117 | 3/1982 | Kaetsu et al. | |
| 4,324,683 | 4/1982 | Lim et al. | |
| 4,391,979 | 7/1983 | Folkman et al. | 424/425 |
| 4,423,099 | 12/1983 | Mueller et al. | 525/905 |
| 4,435,524 | 3/1984 | Dinbergs | 521/65 |
| 4,448,765 | 5/1984 | Ash et al. | |
| 4,477,467 | 10/1984 | Nishizawa et al. | |
| 4,478,818 | 10/1984 | Shell et al. | |
| 4,522,953 | 6/1985 | Barby et al. | 521/64 |
| 4,525,340 | 6/1985 | Lange et al. | |
| 4,542,069 | 9/1985 | Mauz et al. | 526/314 |
| 4,548,990 | 10/1985 | Mueller et al. | 525/123 |
| 4,588,639 | 5/1986 | Ozono | |
| 4,590,068 | 7/1986 | Berthet et al. | 424/81 |
| 4,656,205 | 4/1987 | Walker et al. | 523/201 |
| 4,690,825 | 9/1987 | Won | 424/501 |
| 4,724,240 | 2/1988 | Abrutyn | 514/847 |
| 4,741,872 | 5/1988 | De Luca et al. | 424/486 |
| 4,818,542 | 4/1989 | De Luca et al. | 424/501 |

FOREIGN PATENT DOCUMENTS

| | | | |
|---|---|---|---|
| 0146740 | 3/1985 | European Pat. Off. | 424/501 |
| 0143608 | 5/1985 | European Pat. Off. | |
| 2.692M | 7/1964 | France | |
| 849122 | 9/1960 | United Kingdom | |

OTHER PUBLICATIONS

CA 109-231745(26) Prepn of microsponges for controlled release by suspension polymerization, Sakado Jan. 8, 1987.

*Primary Examiner*—Lester L. Lee
*Attorney, Agent, or Firm*—Townsend and Townsend

[57] ABSTRACT

Active substances intended for topical application are incorporated in novel formulations in which they are retained as impregnants inside the pores of porous solid particles or microspheres. The pores form a continuous network open to the exterior of the particles, permitting outward diffusion of the impregnants at a controlled rate depending on the pore size. The impregnated particles are prepared by impregnation of preformed particles with the active substance.

18 Claims, No Drawings

TWO STEP METHOD FOR PREPARATION OF CONTROLLED RELEASE FORMULATIONS

CROSS-REFERENCE TO RELATED APPLICATIONS

This application is a FILE WRAPPER continuation of application Ser. No. 07/334,051, filed on Apr. 5, 1989, now abandoned, which was a division of application Ser. No. 07/091,641, filed Aug. 31, 1987 now abandoned, the full disclosure of which is incorporated herein by reference, which was a continuation-in-part of applications Ser. No. 06/810,478, filed Dec. 18, 1985 now abandoned; Ser. No. 06/846,321, filed Mar. 31, 1986 now abandond; Ser. No. 06/896,956, filed Aug. 15, 1986 now abandoned; Ser. No. 06/925,081, filed Oct. 30, 1986 now abandoned; Ser. No. 06/925,082 filed Oct. 30, 1986 now abandoned; Ser. No. 06/932,613, filed Nov. 11, 1986 now abandoned; Ser. No. 06/933,243, filed Nov. 21, 1986 now abandoned; Ser. No. 06/936,520, filed Dec. 1, 1986 now abandoned; and Ser. No. 06/940,754, filed Dec. 10, 1986 now abandoned.

BACKGROUND OF THE INVENTION

The present invention relates generally to the preparation of compositions and systems for the topical delivery of active substances to the skin. More particularly, the invention relates to the preparation of a rigid polymer bead delivery system for active substances such as ultraviolet absorbants, insect repellants, steroids, acne treatments, epidermal lipid replacements, counterirritants, hair growth promotents, and the like.

It is frequently desirable to topically deliver active ingredients to the human skin. In many cases, the active ingredients can be applied directly to the skin, either in a substantially pure form or in combination with a liquid vehicle. Such direct application, however, is limited in a number of respects. First, direct application allows rapid evaporation of volatile active substances, such as those listed above. Second, application of the active substances in substantially pure form can often cause toxic and/or allergic reactions, particularly in the case of infrared absorbants, insect repellants and steroids. While such adverse reactions can often be minimized by dilution of the active substance in a suitable liquid carrier, the consequent decrease in concentration frequently limits the effectiveness of the resulting combination for the intended purpose. Finally, many topically applied active substances have undesirable characteristics, such as an oily feel or a strong odor. While dilution of the pure active substance in a suitable liquid carrier can minimize such aesthetic objections, the resulting dilution will also reduce the effectiveness of the final product.

For these reasons, it would be desirable to provide delivery compositions or systems capable of providing controlled and prolonged delivery of active substances after they have been applied to the skin. Desirably, such delivery systems should also control any odor or toxicity which may be associated with the active substance, and should be suitable both for direct application to the skin and for combination in conventional liquid carriers.

Polymeric beads have been proposed for incorporating various active substances. European Patent No. 61,701 describes the preparation of relatively non-rigid polymeric beads for incorporating active substances, exemplified by emollients. Although such polymer delivery system will likely result in prolonged release of an active substance, the non-rigid beads allow the internal pore network incorporating the active substance to collapse as the substance is released, usually resulting in the entrapment and waste of residual active substance. Also, the European patent teaches a preparation procedure which requires the presence of the active substance during the polymerization of the bead material. Such a preparation procedure is unsuitable for heat and/or radiation labile active substances which will be inactivated under the polymerization conditions.

It would therefore be desirable to provide for polymeric bead delivery systems comprising relatively rigid polymeric beads which allow for substantially complete release of the active ingredient from the pore network of the beads. It would be particularly desirable if such bead delivery systems could be prepared prior to the introduction of the active substance so that the active substance is not exposed to relatively harsh polymerization conditions.

SUMMARY OF THE INVENTION

The present invention provides for a polymeric delivery system for a variety of active substances, such as ultraviolet absorbants (sunscreens), insect repellants, steroids, acne treatments, epidermal lipid replacements, counterirritants, hair growth promotents, and the like, which delivery system may be used alone or may be incorporated into a secondary carrier or vehicle composition, or other cosmetic product. The polymeric delivery system with an incorporated active substance is a dry, free-flowing product which can be rubbed directly on the skin, providing for the controlled release of the substance over time. In the more usual situation where the polymeric delivery system is incorporated in another carrier, vehicle, or cosmetic product, use of the delivery system avoids incompatibilities, typically chemical or physical interactions, which might otherwise exist between the substance and other active ingredient(s) in the cosmetic preparation, or between the active substance and the carrier or vehicle itself.

The controlled release of the active substance provided by the polymeric delivery system of the present invention affords a prolonged activity of the substance on the skin. Such prolonged activity reduces the need to frequently reapply the active substance. Additionally, controlled release both reduces any odor which may be associated with the active substance and lessens the possibility of toxicity and allergic reaction resulting from contact of the active substance with the skin.

According to the present invention, the polymeric delivery system is formed by suspension polymerization of suitable monomers in an immiscible phase including a porogen. Generally, the monomers and the porogen are first mixed together and the resulting mixture then suspended in the immiscible phase, usually an aqueous phase. The immiscible phase is then agitated to form droplets of the monomer mixture, and polymerization of the monomer mixture is initiated to form the desired beads from the droplets. Relatively rigid beads having a substantially non-collapsible pore network are formed by providing a cross-linking density of at least about 10%, usually being in the range from about 20% to 80%, more usually being in the range from 25% to 60% cross-linking, and typically being in the range from about 45% to 55% cross-linking. The bead diameter is normally maintained in the range from about 5 microns to 100 microns, usually being about 10 microns to 50 microns, and the total pore volume is in the range from about 0.1 to 2.0 cc/g, usually being in the range from about 0.3 to 1.0 cc/g. The surface area of the beads will range from about 1 to 500 m²/g, usually being in the range from about 20 to 200 m²/g. The precise dimensions and characteristics of the beads are controlled by varying process parameters such as agitation speed and nature of the porogen.

Once the beads are formed, porogen is extracted from the bead product, typically using solvent extraction or evaporation. The desired active substance may then be introduced into the beads, typically by contact absorption, to create the desired final product. In addition to allowing the incorporation of labile active substances, such a two-step preparation process allows greater control over the structure of the bead resulting from a wider choice of porogens and reaction conditions.

DETAILED DESCRIPTION OF THE INVENTION AND PREFERRED EMBODIMENTS

The beads or microspheres used in connection with the present invention are rigid, open-pore, chemically and biologically inert particles with the impregnant held inside the pores by capillary forces. The pores are interconnected and open to the particle surface to an extent that substantially full communication is provided between the internal pore space and the exterior of the particle.

In their most convenient form, the particles are generally spherical in shape, due to the use of suspension polymerization as a preferred method of preparation. While the microspheres may vary widely in size, those falling within the range of about one to about 100 microns in diameter, preferably from about 10 to about 40 microns, will provide the best results. Microspheres within these size ranges are appealing from an aesthetic point of view by imparting a smooth feel to the touch.

The pore dimensions within the spheres may also vary widely, with optimum dimensions depending on the chemical characteristics of the polymers used as well as the diffusive characteristics of the impregnant. Different systems will thus call for different optimum ranges of pore volume distribution to obtain the most desirable properties for the overall formulation. In general, however, best results are obtained with total pore volumes ranging from about 0.01 to about 4.0 cc/g, preferably from about 0.1 to about 2.0; surface areas ranging from about 1 to about 500 m²/g, preferably from about 20 to about 200; and average pore diameters ranging from about 0.001 to about 3.0 micron, preferably from about 0.003 to about 1.0 micron. Following conventional methods of measuring and expressing pore sizes, the pore diameters are calculated from the measurement of the surface area by B.E.T. nitrogen multipoint analysis and from the measurement of the pore volumes by the mercury intrusion method. The calculation is one commonly done by those skilled in the art.

The microspheres are conveniently formed by suspension polymerization in a liquid-liquid system. In general, a solution containing monomers, a polymerization catalyst (if used), and an inert but fully miscible liquid is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid has accordingly served as a porogen, or pore-forming agent, and occupies the pores of the formed beads.

Certain impregnants may serve as the porogen, in which case the porous beads recovered from the suspension immediately after polymerization are substantially ready for use, following removal of surface moisture, and any further processing steps of this nature. In these cases, microsphere formation and incorporation of the impregnant is performed in a single step. This may accordingly be termed a one-step procedure. Those impregnants which are capable of serving as porogens will be liquid impregnants meeting the following criteria:

1. They are either fully miscible with the monomer mixture or capable of being made fully miscible by the addition of a minor amount of non-water-miscible solvent;

2. They are immiscible with water, or at most only slightly soluble;

3. They are inert with respect to the monomers, and stable when in contact with any polymerization catalyst used and when subjected to any conditions needed to induce polymerization (such as temperature and radiation); and 4. They are normally liquids or have melting points below the polymerization temperature. Solids can frequently be converted to liquid form by being dissolved in a solvent or by forming eutectic mixtures.

When using this method, the steps must be performed under an inert atmosphere such as nitrogen. If a polymerization catalyst is used, it must be one which does not oxidize the impregnant, if the latter is susceptible to oxidation. Azo catalysts are examples of such catalysts. Also, polymerization temperatures are best held within a moderate range.

As an alternative to the one-step procedure, the impregnant may be placed inside the pores of preformed dry porous polymer beads. The product is thus prepared in two steps performed in sequence, the polymerization being performed first with a substitute porogen which is then removed and replaced by the squalane or squalene. Materials suitable as substitute porogens will be substances which meet the same four criteria listed above for porogen impregnants.

This covers a wide range of substances. Preferred among these are hydrocarbons, particularly inert, nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes such as toluene and the xylenes. Removal of the porogen may then be effected by solvent extraction, evaporation, or similar conventional operations.

A further advantage of the use of this two-step process is that it permits the removal of unwanted species from the polymerized structures prior to incorporation of the impregnant. Examples of unwanted species include unreacted monomers, residual catalyst, and surface active agents and/or dispersants remaining on the sphere surfaces. A further advantage of this technique is that it permits one to select the amount and type of porogen as a means of controlling the pore characteristics of the finished bead. One is thus no longer bound by the limitations of the impregnant as it affects the structure of the bead itself. This permits partial rather than full filling of the pores with the oil, and further control over pore size and distribution by selection among swelling and non-swelling porogens.

Extraction of the porogen and its replacement with (i.e., impregnation of the dry bead with) the impregnant in the two-step procedure may be effected in a variety of ways, depending on the chemical nature of the porogen and its behavior in combination with that of the other species present. The beads are first recovered from the suspension by filtration, preferably using vacuum filtration apparatus (such as a Buchner funnel). The beads are then washed with an appropriate solvent to remove organic species not bound to the polymer, including surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used i.e., where the porogen, unreacted monomer and water will form an azeotrope. In these cases, steam distillation is an effective way of extracting porogen from the beads. This again may be followed by drying under vacuum.

Once the beads are rendered dry and free of the substitute porogen and any unwanted organic materials, they are impregnated with the impregnant according to conventional techniques. The most convenient such technique is contact absorption. Solid active ingredients are first dissolved in a solvent, and the resulting solution is absorbed by the beads. The solvent may either be retained in the finished product or removed by conventional means such as evaporation or extraction using a further solvent. For those solid ingredients having limited solubility in a particular solvent, high contents in the finished bead can be attained by repeated absorptions each followed by solvent removal.

The polymerization process and the various parameters and process conditions involved in the polymerization can be selected and adjusted as a means of controlling the pore characteristics and consequently the capacity and release characteristics of the ultimate product. For example, proper selection of the cross-linking means, the amount and type of cross-linking agent, and the amount and type of porogen are means of attaining such control. Certain polymerization conditions may also be varied to such effect, including temperature, degree of radiation where used, degree of agitation and any other factors affecting the rate of the polymerization reaction.

Cross-linking in the polymer formation is a major means of pore size control. Monomers which may be polymerized to produce cross-linked polymer beads in accordance with the present invention include polyethylenically unsaturated monomers, i.e., those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer. The polymer beads of the present invention will have greater than 10% cross-linking, preferably from about 10% to about 80% cross-linking, and most preferably from about 20% to about 60% cross-linking. The percentage cross-linking is defined among those skilled in the art as the weight of polyethylenically unsaturated monomer or monomers divided by the total weight of monomer, including both polyethylenically unsaturated and monoethylenically unsaturated monomers.

Monoethylenically unsaturated monomers suitable for preparing polymer beads for the polymer delivery system include ethylene, propylene, isobutylene, diisobutylene, styrene, ethylvinylbenzene, vinylpyridine, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isopropene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The preferred polymer bead of the present invention will be free from reactive groups which will interact with the porogen and the active ingredient which is ultimately incorporated in the composition. In particular, the beads should be free from reactive amino, hydroxyl, carboxylic, and other reactive functionalities. Such beads will not readily undergo unwanted reactions, will be stable over a wide pH range, will resist moderate oxidation and reduction, will be stable at higher temperatures, will resist attack by moisture, and will have a relatively long shelf life.

Particularly preferred polymer delivery systems of the present invention are formed by the copolymerization of styrene and divinylbenzene, vinyl stearate and divinylbenzene, 4-vinylpyridine and ethylene glycol dimethacrylate, or methylmethacrylate and ethylene glycol dimethacrylate. Usually, the monoethylenically unsaturated monomer will be present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings and which is substantially completely free from reactive groups.

Once the microspheres are formed and dried, they are impregnated with the impregnant by contact absorption. As an option, the impregnant may be used in the form of a solution in a suitable organic solvent for purposes of decreasing viscosity and facilitating absorption. Examples of such solvents are liquid petrolatum, ether, petroleum ether, alcohols including methanol, ethanol and higher alcohols, aromatics including benzene and toluene, alkanes including pentane, hexane and heptane, ketones including acetone and methyl ethyl ketone, chlorinated hydrocarbons including chloroform, carbon tetrachloride, methylene chloride and ethylene dichloride, acetates including ethyl acetate, and oils including isopropyl myristate, diisopropyl adipate and mineral oil. After absorption of the solution, the solvent can be evaporated or, if desired, retained inside the pores together with the impregnant. Other formulating materials, such as carriers or adjuvants such as fragrances, preservatives, antioxidants, and other emollients can also be present, and will be incorporated into and onto the beads together with the impregnants and any other materials present.

The impregnant, whether it be pure active ingredient, a mixture of active ingredients or a solution of active ingredient, will generally comprise between approximately 5% and approximately 65% of the total weight of the impregnated beads. When the active ingredient is a potent drug, it will generally be in the form of a dilute solution, and the weight percent of the active ingredient itself will range as low as 0.01% based on the total weight of the impregnated beads.

For topical application, the impregnated beads of the present invention may be used alone or in the form of fluid compositions or preparations similar to those commonly used for skin treatment, for example: gels, creams, lotions, ointments, sprays, powders, or oils. Appropriate vehicles for particular areas or methods of application will be readily apparent to those skilled in the art. When liquid vehicles are used (such as gels, creams, lotions, ointments or oils) and the impregnant is a solution of an active ingredient in a solvent, the solvent and vehicle must be immiscible so that outward diffusion of the active ingredient will not be accelerated by mutual diffusion between the solvent and vehicle. Appropriate combinations will therefore include the combination of a polar solvent and a nonpolar vehicle, and the combination of a nonpolar solvent and a polar vehicle.

The following are some of the considerations specific to various particular types of impregnants, plus examples of preparation and utility. The examples are offered solely for purposes of illustration, and are intended neither to limit nor define the invention in any manner. All parts and percentages are by weight, unless otherwise stated.

1. Adrenocortical Steroid Compositions

Steroids suitable for incorporation in the steroid compositions of the present invention will typically be crystalline powders dissolved in a suitable solvent, typically alcohols, ketones, and other solvents, such as propylene carbonate, as well as the absorption enhancers listed hereinbelow. Typically, the adrenocortical steroid will be present in the solvent at a concentration in the range from about 0.0001% to 5%, more typically in the range from about 0.001% to 2%, more typically in the range from 0.01% to 1.5%, depending on the particular steroid chosen. The concentration of steroid required depends greatly on the nature of the steroid. Adrenocortical steroids suitable for incorporation in the present invention include fluocinolone, fluocinolone acetonide, triamcinolone acetonide, betamethasone valerate, timobesone acetate, hydrocortisone, hydrocortisone acetate, triamcinolone, prednisolone, prednisolone acetate, dexamethasone, beclomethasone dipropionate, betamethasone dipropionate, betamethasone benzoate, clocortolone pivalate, halcinonide, flumethasone pivalate and desonide may also be used.

The steroid compositions of the present invention will typically include an absorption enhancer which promotes the thermodynamic activity and penetrability of the steroid when applied to the skin. Suitable percutaneous absorption enhancers include propylene glycol, propylene carbonate, dialkyl sulfoxides, having up to 22 carbon atoms in each alkyl group, e.g., dimethylsulfoxide, dimethylformamide, dimethylacetamide, diisopropyl adipate, isopropyl myristate, tetrahydrofuran, tetrahydrofurfuryl alcohol, glycerol, N-methyl-2-pyrrolidone, and 1-dodecylhexahydro-2H-azepin-2-one, sold under the tradename Azone. Preferred are the use of propylene glycol, propylene carbonate, and Azone.

The polymeric beads of the steroid composition of the present invention may be incorporated in suitable pharmaceutical carriers into cosmetic preparations. Alternatively, the steroid composition, which is a dry, free-flowing powder, may be utilized by itself without any further incorporation in a carrier of any kind.

The carrier employed in the composition of the present invention should be substantially immiscible with the steroid solution. Petrolatum compounds ranging in viscosity from mineral oil to paraffin waxes are suitable, with a paraffin compound having the approximate consistency of Petrolatum NF (petroleum jelly) being especially preferred as an ointment base. Polysiloxane compounds (also known as silicones) having appropriate viscosity characteristics, usually in the range from about 0.5 to $10^6$ centistokes, are also suitable as carriers. Other suitable materials include adjuvants, such as beeswax, spermaceti, paraffin waxes, fatty acids, alcohols, and amides having from about 10 to 22 carbon atoms; surfactants; thickeners; preservatives; inhibitors; and emulsifiers; may be included with the carrier medium just described. Particularly suitable for use in the present invention is a petrolatum/polysiloxane-based delivery medium described in U.S. Pat. No. 4,017,615, the disclosure of which is incorporated herein by reference.

It has been found that the therapeutic anti-inflammatory activity of fluocinonide-containing beads in a petrolatum-based delivery medium is comparable, based on final weight concentration of the fluocinonide, to that of commercially-available fluocinonide ointments such as Lidex ® (Syntex). Thus, ointments formed using the delivery vehicles of the present invention may employ active ingredient concentration parallel to those of typical ointments, i.e., 0.01% to 1% by weight. It should be noted, however, that therapeutically effective anti-inflammatory compositions may include as little as 0.00001% by weight steroid active ingredient and as much as 5% by weight steroid or higher. A range of 0.01% to 0.2% is particularly useful, with 0.01% to 0.05% being preferred for the more active corticosteroids such as the fluocinonides, and 0.01% to 0.1% being preferred for less active corticosteroids such as the betnovates and the triamcinolones. When polymer beads containing active ingredient are used topically in powder form, therapeutic anti-inflammatory activity may be lower than that of commercial ointments, although activity is increased and/or provided over longer time periods if the polymer beads are rubbed occasionally to promote release of the active ingredient.

Suitable ointments containing polymer beads with active ingredient may be prepared by combining an appropriate amount of the polymer beads with petrolatum and an emulsifier such as Amerchol CAB. To achieve a 0.05% fluocinonide ointment, for example, 4.6 parts by weight (pbw) Amerchol CAB, 32.2 pbw white petrolatum USP (Ultima) and 50.7 pbw white petrolatum USP were first combined and melted, and 12.5 pbw 0.4% fluocinonide polymer beads was then mixed with the melted mixture and cooled. Similarly, a 0.1% ointment was obtained by combining 4.0 pbw Amerchol CAB, 28.4 pbw white petrolatum USP (Ultima) and 42.6 pbw white petrolatum (USP) with 25.0 pbw 0.4% fluocinonide beads. A 0.2% ointment was formulated by combining 2.6 pbw Amerchol CAB, 19.0 pbw white petrolatum (USP) and 28.4 pbw white petrolatum USP with 50.0 pbw 0.4% fluocinonide beads. By starting with polymer beads containing different amounts of active ingredient, the relative weight proportion of polymer bead delivery vehicle can be modulated.

1.1 Experimental

A 2000 ml four-necked reaction flask equipped with a stirrer, condenser, thermometer, and nitrogen inlet was evacuated and charged with nitrogen. 800 ml deionized water, 6.4 grams of gum arabic and 6.4 grams of a lignosulfonate available from the American Can Co. under the trademark Marasperse N-22, were charged into the reaction flask. The mixture was stirred for about 30 minutes. To this mixture was added a freshly prepared solution of 85.6 grams of styrene (99.8% purity), 102.3 grams commercial divinylbenzene (55% divinylbenzene), 5.33 grams benzoyl peroxide (70% active ingredient and 30% water), and 187.9 grams of toluene to serve as a porogen. The phase and solution were agitated by a mechanical stirrer whose stirring rate of about 900–1200 rpm was adjusted to obtain a plurality of droplets having a droplet diameter smaller than about 50 microns. The gum arabic and lignosulfonate serve to stabilize the plurality of droplets. The reaction mixture was heated to about 78° C. while maintaining a constant rate of stirring and passing a slow stream of nitrogen through the reaction vessel. After about 2 hours cross-linking became noticeable. The mixture was stirred another 22 hours at 78° C. and was then allowed to cool to room temperature. The porous polymeric beads were removed from the reaction flask by filtration and washed several times with water to remove gum arabic and lignosulfonate, followed by several washes of isopropanol/acetone mixed solvent (7:3 by volume) and were finally stirred in 400 ml of isopropanol/acetone mixed solvent (7:3) for 20 hours. The polymer was filtered and dried overnight at 65° C. in vacuo. The yield was practically quantitative. The residual monomers such as styrene, DVB and naphthalene were smaller than about 0.01%.

The calculated or theoretical cross-linking density of the purified beads is 30%. This density is calculated by multiplying the weight of divinylbenzene (102.3 g) by the purity of the divinylbenzene (.55) to get the actual weight of pure divinylbenzene which is then divided by the total weight of monomer (102.3 g +85.6 g).

The surface area of a sample of the purified beads was determined by the B.E.T. method to be 1.8 meters$^2$/gram. The B.E.T. method is described in detail in Brunauer, S. Emmet, P. H., and Teller, E., J. Am. Chem. Soc., 60, 309–16 (1938). The surface area of the polymer can be modified by using different porogens such as stable oil compounds which might include, by way of example only, mineral oil, vegetable oils or silicon oils.

The particle size of the beads was determined by an optical microscope to be 60 microns or less with an average approximate particle size diameter of about 10 microns.

The active ingredient fluocinonide (Syntex) was entrapped in the beads described above by exposing the beads to a 1% solution of fluocinonide in propylene carbonate : propylene glycol (7:3) for a period of time sufficient to allow the beads to absorb the active ingredient solution. The amount of active ingredient solution used relative to the amount of polymer beads was adjusted according to the desired final concentration of active ingredient to be contained within the beads. Where a low final concentration is desired, the active ingredient solution was further diluted with a solvent such as acetone, methanol or ethanol prior to combining the solution with the beads in order to achieve a sufficient amount of starting solution to form a slurry with the beads. The diluent solvent was later removed by heating under a vacuum.

To obtain beads with a final active ingredient concentration of 0.05%, 7.6 g of the polymer beads described above was combined with 0.4 g of a 1% solution of fluocinonide in propylene carbonate : propylene glycol (7:3) and 14.8 g acetone. The initial slurry was stirred approximately every five minutes over a period of approximately thirty minutes, during which period the mixture became cake-like and, finally, powder-like in consistency. The resulting powder was then oven-dried for approximately three hours at 40°–60° C. and 25 mmHg, at which point the powder had reached a constant weight and the acetone has been removed. Similarly, a 0.25% formulation was prepared by mixing 4.8 g polymer beads, 3.2 g steroid solution and 6.4 g acetone, as described above.

The efficacy of the polymer bead delivery vehicle of the present invention was demonstrated for both the powder and ointment forms of the beads using a vasoconstriction assay. This method is based on the Stoughton-McKenzie vasocontriction assay for corticosteroid formulations (McKenzie, A. W., and Stoughton, R. B., "Method for Comparing Percutaneous Absorption of Steroids," Arch. Dermatol., 86, 608–10 (1962)). All test preparations were placed in identical containers, coded and assigned by random tables to individual test sites. The test subjects were normal adult male and female volunteers not receiving any steroids and who had not participated in any studies using steroids for at least four weeks prior to testing. The forearms of the subjects were prepared by gentle washing and drying. Strips of double-adhesive coated Blenderm ® tape with 7×7 mm prepunched squares (3M) are applied to each forearm to isolate the application sites. An appropriate dose of the test formulation (either 2 mg or 3 mg) was then applied to the skin in each square and was spread and rubbed with consistent pressure using a clean HPLC vial at each application site. In cases where powder-form polymer beads containing fluocinonide was used, the forearm was inverted after application and each individual site was gently brushed with a clean square of gauze to remove excess polymer beads. A protective cage was applied over the sites on the forearm designated for "open" application. On the other arm ("occluded") the sites were covered with Saran Wrap ®, the margins sealed with tape and a protective cage placed over the sites. After six hours of exposure of the skin to the corticosteroid preparations, all the tapes were removed and the forearms were washed.

Scoring in the assay was preformed by two experienced observers who independently scored the presence or absence of vasoconstriction and the degree and blanching at 8, 24 and 32 hours after the time of application of the formulations to the sites.

As evidenced in Table 1, the powder form polymer bead formulations of the present invention achieved significant vasoconstriction as compared to commercially-supplied Lidex ® fluocinonide ointment (Syntex) not using a polymer bead delivery vehicle. Although vasoconstriction due to the powder form polymer beads was somewhat less than that observed with the Lidex ® ointment, this difference might have been due to the fact that excess powder formulation was brushed off after application to the forearms. Table 1.1 demonstrates that intermittent rubbing of the powder-form formulations acted to promote and prolong vasoconstriction activity. Table 1.2 demonstrates that the polymer bead delivery vehicle of the present invention, when applied in an ointment form comparable to that of commercially-supplied fluocinonide ointment, achieved a level of vasoconstriction approximately equal to that of the commercially-supplied product. This effect is achieved independent of any rubbing of the polymer bead ointment subsequent to application. It may be expected that such rubbing will further enhance vasoconstriction activity attributable to the delivery vehicle of the present invention.

TABLE 1

Vasoconstriction Assay Readings-
Polymer Powder Formulations

| FLUOCINONIDE FORMULATION | Hours After Application | | | |
|---|---|---|---|---|
| | 8 | 24 | 32 | Total % |
| Polymer Beads (0.4%) Occluded Application: | | | | |
| Sites Responding (%): | 50.0 | 62.5 | 50.0 | 162.5 |
| Intensity of Response (%): | 22.9 | 22.9 | 16.7 | 62.5 |
| Polymer Beads (0.4%) Open Application: | | | | |
| Sites Responding (%): | 62.5 | 56.3 | 25.0 | 143.8 |
| Intensity of Response (%): | 25.0 | 18.8 | 8.3 | 52.1 |
| Ointment (0.05%) Occluded Application: | | | | |
| Sites Responding (%): | 100.0 | 87.5 | 75.0 | 262.5 |
| Intensity of Response (%): | 72.9 | 33.3 | 27.1 | 133.3 |
| Ointment (0.05%) Open Application: | | | | |
| Sites Responding (%): | 93.8 | 100.0 | 93.8 | 287.6 |
| Intensity of Response (%): | 68.8 | 39.6 | 31.3 | 139.7 |

NOTE: Dosage was 2 mg of polymer powder, with entrapped fluocinonide (0.4%), or 2 mg Lidex ® 0.05% fluocinonide ointment. Test sites were rubbed at time zero, washed at time 6 hours, and read at the times indicated.

TABLE 1.1

Effect of Re-Rubbing on Vasoconstriction
Effect of Polymer Powder Formulations

| FLUOCINONIDE FORMULATION | Hours After Application | | | |
|---|---|---|---|---|
| | 8 | 24 | 32 | Total % |
| Polymer Beads (0.5%) | | | | |
| Sites Responding (Increase %) | 25.0 | 12.5 | 31.3 | 62.8 |
| Intensity of Response (Increase %) | 8.3 | 4.1 | 10.4 | 22.8 |
| Polymer Beads (0.25%) | | | | |
| Sites Responding (Increase %) | 0 | 31.3 | 31.3 | 62.6 |
| Intensity of Response (Increase %) | 0 | 10.4 | 12.5 | 22.9 |
| Polymer Beads (0.4%) | | | | |
| Sites Responding (Increase %) | −18.7 | 12.5 | 25.0 | 18.8 |
| Intensity of Response (Increase %) | −10.4 | 4.1 | 10.4 | 4.1 |

NOTE: Dosage was 2 mg of polymer powder, with entrapped fluocinonide at indicated proportion. All test sites were left open (unoccluded) and were rubbed and brushed off at time zero. Control powder sites were washed at time 6 hours; re-rubbed powder sites were re-rubbed at 6, 8, and 24 hours. Readings were made at times indicated. Data represents percent readings taken at re-rubbed sites minus percent readings taken at corresponding control sites.

TABLE 1.2

Vasoconstriction Assay Readings-
Polymer-in-Ointment Formulations

| FLUOCINONIDE FORMULATION | Hours After Application | | | |
|---|---|---|---|---|
| | 8 | 24 | 32 | Total % |
| Polymer Beads (0.05% in Ointment-Occluded) | | | | |
| Sites Responding (%) | 87.5 | 68.8 | 81.3 | 237.6 |
| Intensity of Response (%) | 75.0 | 29.2 | 29.2 | 133.4 |
| Polymer Beads (0.05% in Ointment-Open) | | | | |
| Sites Responding (%) | 87.5 | 62.5 | 68.8 | 218.8 |
| Intensity of Response (%) | 72.9 | 20.8 | 25.0 | 118.7 |
| Polymer Beads (0.1% in Ointment-Occluded) | | | | |
| Sites Responding (%) | 87.5 | 62.5 | 68.8 | 218.8 |
| Intensity of Response (%) | 66.7 | 25.0 | 22.9 | 114.6 |
| Polymer Beads (0.1% in Ointment-Open) | | | | |
| Sites Responding (%) | 93.8 | 75.0 | 81.3 | 250.1 |
| Intensity of Response (%) | 72.9 | 27.1 | 29.2 | 129.2 |
| Polymer Beads (0.2% in Ointment-Occluded) | | | | |
| Sites Responding (%) | 75.0 | 81.3 | 81.3 | 237.6 |
| Intensity of Response (%) | 58.3 | 29.2 | 29.2 | 116.7 |
| Polymer Beads (0.2% in Ointment-Open) | | | | |
| Sites Responding (%) | 93.8 | 62.5 | 37.5 | 193.8 |
| Intensity of Response (%) | 68.8 | 25.0 | 12.5 | 106.3 |
| Commercial Ointment (0.05%-Occluded) | | | | |
| Sites Responding (%) | 93.8 | 68.8 | 68.8 | 231.4 |
| Intensity of Response (%) | 79.2 | 27.1 | 22.9 | 129.2 |
| Commercial Ointment (0.05%-Open) | | | | |
| Sites Responding (%) | 87.5 | 75.0 | 87.5 | 250.0 |
| Intensity of Response (%) | 77.1 | 27.1 | 33.3 | 137.5 |

NOTE: Dosage was 3 mg of petrolatum-based ointment containing polymer powder, with entrapped fluocinonide at indicated proportion, or 3 mg Lidex ® 0.05% fluocinonide ointment. Test sites were rubbed at time zero, washed at time 6 hours, and read at the times indicated.

TABLE 1.3
Demand and Sustained Release of Corticosteroid Solution from Beads Measured by Vasoconstrictor Response

| TIME (HOURS AFTER APPLI- CATION) | CORTICOSTEROID* CONCENTRATION | | | |
|---|---|---|---|---|
| | 0.05% | | 0.25% | |
| | APPLICATION | | | |
| | Initial Application Only | Reactivate at 6, 8, 24 Hours | Initial Application Only | Reactivate at 6, 8, 24 Hours |
| | RESPONSE PERCENT | | | |
| 8 | 12.5 | 37.5 | 0 | 0 |
| 24 | 12.5 | 25 | 0 | 31.3 |
| 32 | 0 | 31.3 | 12.5 | 43.8 |

Corticosteroid Solution in polymer delivery systems applied to both arms and excess removed.
Application sites reactivated again on one arm at 6, 8, and 24 hours.
Corticosteroid Solution release and effect measured by vasoconstrictor response at 8, 24, and 32 hours.
*Fluocinonide.

In an additional study, fluocinonide was dissolved in a 30/70 propylene glycol/propylene carbonate system and entrapped in the microsponge sponge entrapment system in accordance with the present invention. The degree of vasoconstriction produced served as an indicator of the release of the corticosteroid solution from the microsponge entrapment system. Equal amounts of the microscopic sponge particles were directly applied to human forearms, rubbed gently, and the excess powder brushed off. On one arm, no further application or manipulation was made. On the other arm, the site of initial application was gently rubbed at 7, 23, and 31 hours, but no additional product was added.

Vasoconstriction responses were measured and recorded at 8, 24, and 32 hours and the results are presented in Table 1.3. The increased and continued vasoconstriction produced in the arm that was rubbed several times is definitive evidence of the demand and sustained release of the corticosteroid solution from the microsponge entrapment system.

2. Topical Formulations for the Promotion of Hair Growth

For topical application, the impregnated beads of the present invention may be used alone or in the form of fluid compositions or preparations similar to those commonly used for skin treatment, for example: gels, creams, lotions, ointments, sprays, powders, or oils. Appropriate vehicles for particular impregnants or areas or methods of application will be readily apparent to those skilled in the art.

Minoxidil, the preferred hair growth promotion agent, is a solid soluble in propylene glycol, and may only be incorporated into the beads by the two-step process.

2.1 Example

A 2000 ml four-necked reaction flask equipped with a motorized stirrer, reflux condenser, thermometer, and nitrogen inlet were evacuated and purged with nitrogen. 800 parts of deionized water, 6.4 parts of gum arabic and 6.4 parts of a lignosulfonate available from Reed Lignins, Inc., under the trademark Marasperse N-22, were charged to the reaction flask. The mixture was stirred for about 30 minutes at about 50° C. until the dispersants (gum arabic and lignosulfate) dissolved to form an aqueous phase.

To this mixture was added a freshly prepared solution of 85.6 parts of styrene (99.8% purity), 102.3 parts of commercial divinylbenzene (55.6% divinyl benzene, 42.3% ethylvinylbenzene), 5.3 parts of benzoyl peroxide (70% active ingredient and 30% water), and 187.9 parts of toluene to serve as a porogen. The aqueous phase and organic solution were agitated by stirring at a rate adjusted to give a plurality of droplets having an average droplet diameter of about 10–60 microns, as determined by visual observation of a sample of the droplets with an optical microscope (400X) with the droplets being stabilized by the dispersants. This rate was approximately 1200 rpm. The reaction mixture was heated to about 78° C. and constantly stirred while a slow stream of nitrogen is passed through the reaction vessel, thus forming porous beads of cross-linked styrene/divinylbenzene copolymer having heptane entrapped within the network of pores. The mixture was stirred another 22 hours at 78° C. and allowed to cool to room temperature. The mixture was then diluted with 200 parts of water, and the porous polymeric beads were removed from the reaction flask by filtration. The filtered beads were washed initially three times with one liter portions of deionized water to remove the dispersants, followed by several washes of isopropanol/acetone mixture (7:3, respectively, by weight) to remove any residual, unreacted monomer and the heptane used as the porogen during polymerization. The beads were filtered and then dried at 65° C. in vacuo.

The calculated or theoretical cross-linking density of the purified beads was 30%. This density is calculated by multiplying the weight of divinylbenzene (102.3 g) by the purity of the divinylbenzene (0.55) to et the actual weight of pure divinylbenzene which is then divided by the total weight of monomer (102.3 g + 5.6 g).

The surface area of a sample of the purified beads was determined by the B.E.T. method to be 1.8 meters$^2$/gram. The B.E.T. method is described in detail in Brunauer, S. Emmet, P. H., and Teller, E., *J. Am. Chem. Soc.*, 60, 309–16 (1938).

The particle size of the beads was determined by an optical microscope to be 60 microns or less with an average approximate particle size diameter of about 10 microns.

Minoxidil was obtained from Minoxidil 10 mg tablets (Upjohn, Loniten Tablet, 10 mg) by an ethanol extraction in which Minoxidil tablets were first ground into a powder. 3.4 grams of the ground powder were then mixed with 15 ml of ethanol (95% ethanol and 5% ispropyl alcohol) and the resultant mixture was stirred for 10 minutes. The mixed solution produced by stirring was then filtered and the ethanol was evaporated. 0.35 g of white Minoxidil solid, which shall be referred to as CH 215M, was obtained.

In a first example of preparation of polymeric beads having a solution of an active ingredient useful for promoting hair growth dissolved in a percutaneous absorption enhancer held within a network of pores of the polymeric beads, 10.6 mg of the white Minoxidil solid CH 215M was dissolved in 2 grams of a 50:50 solution of propylene carbonate/ethanol. 1.5 grams of the polymeric beads CH 215 was then mixed into the solution until the product is homogeneous. The Minoxidil content in the resulting product, which shall be referred to as CH 215 A-3, was 3 mg/g. In a second example, 1.2 parts of the white Minoxidil solid CH 215M, was added to 32.1 parts of propylene glycol and stirred in a flask at 45° C. until the white Minoxidil solid CH 215M was completely dissolved. Thereafter, 61.7 parts of polymeric beads (CH 215) were added to the solution which was mixed until the product is homogeneous. The Minoxidil content in the resulting product was is 12 mg/g.

A composition useful in the method of the present invention is then prepared by adding 9.09 parts of CH 215 A-3 to 90.01 parts of a medium comprised of petroleum jelly. The product was then mixed until homogeneous. The Minoxidil content in the resulting product was 1.1 mg/g. This product could then be rubbed into portions of the skin and scalp to enhance hair growth.

While the above description has described the preparation of a composition useful in the method of the present invention to promote hair growth, it should be noted that a product containing higher concentrations of Minoxidil could be used to achieve the known cardiovascular effects of Minoxidil. Thus, for example, such a product could be rubbed onto the skin to provide a topical application of Minoxidil, as opposed to an oral dosage, for use in controlling hypertension.

3. Insect Repellent Compositions

Insect repellent substances suitable for incorporation into the compositions of the present invention will function through volatilization and formation of a thin protective barrier or layer as the repellent is released from the polymer delivery system. The repellent substances will usually be liquids, although solids which are dissolved or dispersed in a liquid carrier may also find use. The substances should be generally non-toxic, at least when incorporated in the polymer delivery system, and should be effective against a wide variety of insects. Insect repellent substances which are presently accepted as safe and which are suitable for use in the present invention are set forth in Table 3.

TABLE 3

| Group | Exemplary Compounds |
|---|---|
| Terpenoids | Citronellal |
| | Geraniol |
| | Terpentine |
| | Pennyroyal |
| | Cedarwood |
| | Eucalyptus |
| | Wintergreen |
| Benzoquinones | Benzquinone and its homologs, methyl ether derivatives and homologs |
| Aromatics | Cresols |
| | Benzaldehyde |
| | Benzoic acids |
| Synthetics | N,N-diethyl-$\underline{m}$-toluamide (deet) |
| | Ethyl hexanediol |
| | Dimethyl phthalate |
| | Dimethyl ethyl hexanediol carbate |
| | Butopyronoxyl |
| | Di-$\underline{n}$-propyl isocinchonmeronate |
| | N-Octyl bicycloheptene dicarboximide |
| | 2,3,4,5-bis(2-butylene)tetrahydro-2-furaldehyde |

The insect repellent substances listed in Table 3 may be used alone, or more desirably, in combinations tailored to be effective against a greater variety of insects than a single repellent alone. Generally, it will be easier to combine different inset repellent substances inside the polymer delivery system of the present invention than it would be combining them by themselves or in liquid vehicles or carriers. Insect repellent substances which would tend to separate because of physical differences, e.g., immiscibility, may be held within the polymer delivery system in a dispersion or mixture which helps assure that they will be released at substantially the same rate over time.

The insect repellent composition of the present invention may be incorporated in a suitable vehicle, carrier or into cosmetic preparations, such as body powders, sunscreen and sun tanning lotions, body lotions, and the like. In some cases, it may be desirable to include both absorbed and unabsorbed insect repellent substance in the same composition. This has the advantage that a portion of the repellent will be available immediately, while the remaining repellent will be released over time. Alternatively, the insect repellent composition, which is a dry, free-flowing powder, may be utilized by itself without further incorporation in a carrier or vehicle of any kind. Usually, the insect repellent substance will comprise from about 5% to 65% by weight of the insect repellent composition, more usually comprising from about 20% to 60% by weight, and typically including in the range from about 40% to 55% by weight.

The polymeric beads prepared as just described function as a reservoir for controlled delivery of the retained insect repellent substances providing a wide range of advantages over the conventional formulations. Release of the insect repellent substances from the pores occurs in sustained manner, providing a continuous fresh supply of active substance to the epidermal area to which the preparation has been applied. These liquids diffuse out of the pores into either the vehicle if one is used or the natural bodily secretions present on one's skin at the applied area, in accordance with known principles of the diffusion of one liquid through another. The activity-time curve of the insect repellent substance is thus extended and flattened out. The magnitude of the release rate is controlled by the pore volume distribution in the bead itself, notably the total pore volume and the average pore diameter. Selection of the values of these parameters according to predetermined standard provides control of the release rate to desired levels.

3.1 Example

A 2000 ml four-necked reaction flask equipped with a motorized stirrer, reflux condenser, thermometer, and nitrogen inlet was evacuated and purged with nitrogen. 900 Parts of deionized water, 7.2 parts of gum arabic and 7.2 parts of a sodium-based lignosulfonate (Reed lignin) available from the American Can Co. under the trademark Marasperse N-22, were charged to the reaction flask. The mixture was heated, with stirring, in an oil bath at about 50 degrees Celsius until the dispersants (gum arabic and lignosulfate) dissolved to form an aqueous phase.

To this mixture there was then added a freshly prepared solution of 143.3 parts of styrene (99.8% purity), 44.6 parts of commercial divinylbenzene (55.6% divinyl benzene, 42.3% ethylvinylbenzene), 7.7 parts of benzoyl peroxide (70% active ingredient and 30% water), and 144 parts of toluene (porogen). The aqueous phase and organic solution were agitated by stirring at a rate adjusted to give a plurality of droplets having an average droplet diameter of about 10–60 microns, as determined by visual observation of a sample of the droplets with an optical microscope (400X) with the droplets being stabilized by the dispersants. The reaction mixture was then heated to about 95° C. and maintained at that temperature for about 20 hours, at the previously adjusted stirring rate, to form porous beads of cross-linked styrene/divinylbenzene copolymer having toluene entrapped within the network of pores. The mixture was then cooled and the porous polymeric beads were removed from the reaction flask by filtration. The filtered beads were washed initially three times with one liter portions of deionized water to remove the dispersants, followed by three washes with one liter portions of isopropanol to remove any residual, unreacted monomer and the toluene used as the porogen during polymerization. The beads were then dried in an oven at 70° C. for six hours. The average particle diameter of these beads was 10 microns, as measured by optical microscopy.

The calculated or theoretical cross-linking density of the purified beads is 13%. This density is calculated by multiplying the weight of divinylbenzene (44.6 parts) by the purity of the divinylbenzene (0.556) to get the actual weight of pure divinylbenzene which is then divided by the total weight of monomer (144.3 parts +44.6 parts) and multiplied by 100.

The surface area of a sample of the purified beads was determined by the B.E.T. method to be 1.1 meters$^2$/gram while the pore volume was determined by the mercury intrusion method to be 0.0195 ml/gram. The B.E.T. method is described in detail in Brunauer, S. Emmet, P. H., and Teller, E., *J. Am. Chem. Soc.*, 60, 309–16 (1938).

3.2 Example

By repeating the procedure of Example 3.1 in every essential detail, except for the weights of monomers employed, macroporous cross-linked polymer beads having the following characteristics were obtained:

| | |
|---|---|
| Styrene, parts | 85.6 |
| Divinylbenzene, parts | 102.3 |
| Porogen, parts Toluene, | 188 |
| Calculated Cross-Linking Density, % | 30 |
| Average Particle Diameter, m | 25 |
| Surface Area, M$^2$/g | 1.8 |
| Pore Volume, ml/g | 0.04 |

3.3 Example

A 15 part portion of the macroporous cross-linked polymer beads prepared as described in each of Examples 3.1 and 3.2 above was mixed at room temperature with a 60 part portion of diethyl-m-toluamide, and the resulting suspensions were stirred at about 100 rpm for 24 hours in a closed container.

The suspensions were then filtered and the filtrates washed three times with an aqueous detergent solution (Triton), then three times with deionized water. The washed beads were then oven-dried at 70° C. for 6 hours, and their diethyl-m-toluamide contents were determined by acetone extraction (Sohxlet) to be 45%.

3.4 Example

A 0.5 part sample of the diethyl-m-toluamide containing beads of Example 3.3, on a sheet of filter paper, and a sheet of filter paper impregnated with an equivalent amount of diethyl-m-toluamide, were heated under a vacuum of 25 inches of mercury at 100° C. for 10 hours, during which time the percentage weight loss of diethyl-m-toluamide was determined each hour by weighing the bead and filter paper samples. The results of these weight loss determinations are shown graphically in FIG. 1, and demonstrate that a high degree of sustained release can be achieved using the polymeric delivery systems of this invention.

4 Topical Compositions used in the Treatment of Acne

Substances active as acne treatment agents which can be used in the present invention include benzoyl peroxide, salicylic acid and resorcinol. Benzoyl peroxide and salicylic acid are preferred. Benzoyl peroxide may not be used as a porogen, although salicylic acid may. In general, the two-step process is preferred for these substances.

4.1 Example

A 2000 ml four-necked reaction flask equipped with a motorized stirrer, reflux condenser, thermometer, and nitrogen inlet was evacuated and purged with nitrogen. 800 parts of deionized water, 6.4 parts of gum arabic and 6.4 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 102.3 parts of styrene (99.8% purity), 85.6 parts of commercial divinylbenzene (55.6% divinyl benzene, 42.3% ethylvinylbenzene), 5.3 parts of benzoyl peroxide (70% active ingredient and 30% water), and 130 parts of heptane. The aqueous phase and organic solution were agitated by stirring at a rate adjusted to give a plurality of droplets having an average droplet diameter of about 10–60 microns, as determined by visual observation of a sample of the droplets with an optical microscope (400X) with the droplets being stabilized by the dispersants. This rate is approximately 1200 rpm. The reaction mixture was then heated to about 80° C. and maintained at that temperature for about 20 hours, at the previously adjusted stirring rate, to form porous beads of cross-linked styrene/divinylbenzene copolymer having heptane entrapped within the network of pores. The mixture was then cooled, diluted with 200 parts of water, and the porous polymeric beads were removed from the reaction flask by filtration. The filtered beads were washed initially three times with one liter portions of deionized water to remove the dispersants, followed by three washes with 0.6 liter portions of isopropanol: acetone mixture (7:3, respectively, by weight) to remove any residual, unreacted monomer and the heptane used as the porogen during polymerization. The beads were then dried in an oven at 80°–100° C. for eight hours.

The average particle diameter of these beads was 25 microns, as measured by a Sedimentation Micromeritics Microsizer 5300, an instrument available from Micromeritics Instrument Company, Norcross, Ga. The particle diameter determination method is described in detail in the "Microsizer 5300 Particle Size Analyzer Instruction Manual" (1984) associated with the instrument.

The calculated or theoretical cross-linking density of the purified beads is 25%. This density is calculated by multiplying the weight of divinylbenzene (85.6 parts) by the purity of the divinylbenzene (55.6%) to get the actual weight of pure divinylbenzene which is then divided by the total weight of monomer (85.6 parts +102.3 parts) and multiplied by 100.

The surface area of a sample of the purified beads was determined by the B.E.T. nitrogen multipoint analysis to be 91.2 m$^2$/g while the pore volume was determined by the mercury intrusion method to be 1.0 cc/g. The B.E.T. method is described in detail in Brunauer, S., Emmet, P. H., and Teller, E., *J. Am. Chem. Soc.*, 60, 309–16 (1938). The mercury intrusion method is described in detail in "Advanced Experimental Techniques in Powder Metallurgy," pages 225-252, (Plenum Press, 1970).

4.2 and 4.3 Examples

By repeating the procedure of Example 4.1 in every essential detail, except for the weights of monomers and porogen employed, porous cross-linked polymer beads were obtained having the following characteristics listed in Table 4.1:

TABLE 4.1

| Example | Ratio Of Parts Styrene/Divinyl-Benzene/Porogen | Calculated CrossInkng Density, % | Avg. Particle Diam, μm | Surface Area $m^2/g$ | Pore Volume ml/g |
|---|---|---|---|---|---|
| 2 | 89/100/180 (porogen = mineral oil) | 29 | 25 | 75 | 1.36 |
| 3 | 85.6/102.3/188 (porogen = toluene) | 30 | 25 | 1.8 | 0.04 |

4.4 Example

A 10 part portion of the macroporous cross-linked polymer beads prepared as described in each of Examples 4 1 4.3 above was mixed at room temperature with 16 parts of a 12.5% solution of benzoyl peroxide in acetone, and the resulting suspensions were hand-stirred for a few minutes. The thus-obtained homogeneous wet powders were washed three times with 30 ml portions of deionized water in a funnel, then air dried at room temperature for 20 hours. The benzoyl peroxide contents entrapped within these beads' macropores as determined by titration with iodine in isopropanol and based on the total weight of beads and entrapped benzoyl peroxide, were as follows:

TABLE 4.2

| Beads Of Example | Wt Of Water, % | Wt. Of Benzoyl Peroxide, % |
|---|---|---|
| 1 | 1 | 12.2 |
| 2 | 1 | 12.1 |
| 3 | 8 | 9.6 |

4.5 Example

Two 10 part portions of the macroporous cross-linked polymer beads prepared as described in Example 4.1 above were mixed at room temperature with a 14 part portion of a 12.5% solution of benzoyl peroxide in acetone and a 10 part portion of a 20% solution of salicylic acid in acetone, respectively. The resulting wet powders were hand-stirred until homogeneous, then air-dried at room temperature for 20 hours. Their respective contents of benzoyl peroxide and salicylic acid, as determined by titration with iodine and dilute aqueous sodium hydroxide, respectively, and based on the total weight of beads and entrapped benzoyl peroxide and salicylic acid, were:

| Benzoyl peroxide | 11.3% |
|---|---|
| Salicylic acid | 16% |

The two lots of beads were then commingled to provide a therapeutic delivery system for topically applying benzoyl peroxide and salicylic acid together to the skin.

Fragrance Compositions

Fragrant substances useful in the fragrance compositions of the present invention include the following general classes:

| Class | Examples |
|---|---|
| (1) Flower oils obtained from cultivated flowers, usually by steam distillation or solvent extraction. | Rose, lilac, jasmine, apple blossoms, lavender, carnation, wisteria, and ylang. |
| (2) Essential oils obtained from plant parts, such as roots, barks, leaves, fruits, and the like, usually by steam distillation. | Sandalwood, vetivert, oakmoss, bergamot, rosewood, patchouli, orris, citrus oils, and citronella, sage, fern, and spice. |
| (3) Substances of animal origin. | Musk, ambergris, civet, castoreum, etc. |
| (4) Chemical compounds isolated from naturally-occurring substances. | Geraniol and citronellel |
| (5) Synthetic substances, including substances mimicking natural substances and compounds, and substances which are not related to natural substances. | Phenyl ethyl alcohol, methyl benzoate, benzaldehyde, benzyl salicylate, musk ambrette, ethyl acetate, and ethyl brassylate. |
| (6) Resinoids | Styrax, benzoin, myrrh, olibanum, opoponax, and galbanum. |

The fragrant substances may be used individually or, more typically, will be combined to achieve a desired aroma prior to incorporation in the fragrance compositions of the present invention. The fragrant substances may also be dissolved in a suitable liquid, such as an alcohol, ester, or other organic solvent, or used without dilution, depending on the physical characteristics of the fragrance and desired strength of the fragrant composition. Many of the oils will be suitable for use as the porogen without dilution, while it will often be desirable to dissolve the fragrant substance if it is desired to attenuate the aroma.

Once the fragrance compositions have been prepared, by either the one-step or two-step procedures described above, it may be used alone or further incorporated in a carrier or vehicle or in virtually any type of product where it is desired to impart an aroma. The composition may be used alone as a perfume by simply applying the composition, which is a dry powder, to the skin. The composition may also be incorporated in a suitable carrier or vehicle, typically an alcohol, and used as a perfume.

More commonly, the fragrance compositions of the present invention will be incorporated in other products in order to impart a fragrance. For example, the composition is ideally suited for combining with other powders, such as body powders, foot powder, and the like, by simple mixing. The fragrant compositions may also be incorporated into a wide variety of other products, such as soaps, detergents, paper goods, and the like, by introducing the composition at the appropriate point in the fabrication procedure.

5.1 Example

A 2000 ml four-necked reaction flask equipped with a motorized stirrer, reflux condenser, thermometer, and nitrogen inlet was evacuated and purged with nitrogen. 800 part of deionized water, 6.4 parts of gum arabic and 6.4 parts of sodium-based lignosulfonate (Reed lignin) available from the American Can Co. under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 85.6 parts of styrene (99.8% purity), 102.3 parts of commercial divinylbenzene (55.6% divinyl benzene, 42.3% ethylvinylbenzene), 5.3 parts of benzoyl peroxide (70% active ingredient and 30% water), and 188 parts of toluene (porogen). The aqueous phase and organic solution were agitated by stirring at a rate adjusted to give a plurality of droplets having an average droplet diameter of below about 60 microns, as determined by visual observation of a sample of the droplets with an optical microscope (400X) with the droplets being stabilized by the dispersants. This rate was approximately 1000 rpm. The reaction mixture was then heated to about 78° C. and maintained at that temperature for about 20 hours, at the previously adjusted stirring rate, to form porous beads of cross-linked styrene/divinylbenzene copolymer having toluene entrapped within the network of pores. The mixture was then cooled, diluted with 1000 parts of water, and the porous polymeric beads removed from the reaction flask by filtration. The filtered beads were washed initially three times with one liter portions of water to remove the dispersants, followed by three washes with one liter portions of acetone to remove any residual, unreacted monomer and the toluene used as the porogen during polymerization. The beads were then dried in an oven at 70° C. for 10 hours. These beads were white and opaque in appearance, indicating the microporosity, and had an average particle diameter of less than 50 microns. They had a pore volume of 0.04 ml/g as measured by a mercury intrusion porosimeter.

The calculated or theoretical cross-linking density of the purified beads was 30%. This density was calculated by multiplying the weight of divinylbenzene (102.3 parts) by the purity of the divinylbenzene (0.556) to get the actual weight of pure divinylbenzene which was then divided by the total weight of monomer (85.6 parts + 102.3 parts) and multiplied by 100.

The surface area of a sample of the purified beads was determined by the B.E.T. method to be 1.8 meters$^2$/gram while the pore volume was determined by the mercury intrusion method to be 0.04 ml/gram. The B.E.T. method is described in detail in Brunauer, S. Emmet, P. H., and Teller, E., J. Am. Chem. Soc., 60:309–16 (1938). The mercury intrusion method is described in detail in "Advanced Experimental Techniques in Powder Metallurgy", pages 225–252 (Plenum Press, 1970).

5.2 Example

A two liter four-necked reaction flask equipped as described in Example 5.1 was evacuated and purged with nitrogen. An aqueous phase made up of 800 parts of deionized water, 8 parts of gum arabic and 8 parts of Marasperse N-22 was added to the flask, and an organic solution made up of 100 parts of methyl methacrylate, 100 parts of ethylene glycol dimethacrylate, 10 parts of butyl methacrylate, 2 parts of lauroyl peroxide and 173 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets being stabilized by the dispersants.

The reaction mixture was then heated to 80° C. and maintained at that temperature for 6 hours while maintaining a nitrogen flow of 1 ml/minute, to form porous beads of cross-linked methyl methacrylate/butyl methacrylate/ethylene glycol dimethacrylate terpolymer having toluene entrapped within the pores. The reaction mixture was then cooled and the beads were collected by filtration, washed three times with 1000 parts of water, and three times with 1000 parts of isopropanol, and then dried in air at room temperature.

The calculated or theoretical cross-linking density of the purified beads was 47.6%, and was calculated by dividing the weight of ethylene glycol dimethacrylate (100 parts) by the total weight of monomer 210 parts +(100 parts +110 parts) and then multiplying by 100.

The surface area of a sample of the purified beads was 52 meters$^2$/gram and the pore volume was 0.4 ml/gram, determined as described in Example I above.

5.3 5.6 Examples

By repeating the procedure of Example 5.1 in every essential detail except for the weights of monomers employed and, in one case, the porogen used, the macroporous cross-linked polymer beads described in Table 5.1 below were obtained.

TABLE 5.1

| Example | Methyl Methacrylate | Ethylene Glycol Dimethacrylate | Porogen Parts | Calculated Cross-linking Density | Average Particle Diameter, um | Surface Area m$^2$/g | Pore Volume ml/g |
|---|---|---|---|---|---|---|---|
| 3 | 100 | 100 | 173[1] | 50% | 25 | 73.8 | 0.405 |
| 4 | 150 | 150 | 450[1] | 50% | 15 | 95.8 | 0.508 |
| 5 | 100 | 100 | 200[1] | 50% | 25 | 84.0 | 0.38 |
| 6 | 210 | 90 | 200[2] | 30% | 15 | 2.34 | 0.58 |

[1]Toluene
[2]Heptane

5.6 Example

A 5 part portion of the macroporous cross-linked polymer beads prepared as described in each of Examples 5.1 and 5.2 above were hand mixed at room temperature with a 5 part portion of Christmas tree air freshener fragrance (H&R A670201). The fragrance content of the beads was determined to be 50%.

A 1 part sample of each batch of fragrance containing beads, together with a 0.5 part sample of unabsorbed fragrance absorbed on filter paper, were held in air at room temperature (about 25° C.) and atmospheric pressure for 24 hours, during which time the percentage weight loss by weighing the bead and filter paper samples. The results of these weight loss determinations demonstrated that a high degree of sustained release over a longer period of time was achieved using the polymeric fragrance delivery systems of this invention.

5.7 Example

Six-part portions of the macroporous cross-linked polymer beads of Examples 5.5 and 5.6 are mixed with four parts of methyl benzoate fragrance. The fragrance content of the beads is calculated to be 40%.

6 Ultraviolet Absorbing Substances

UV absorptive materials suitable for the present invention will be solids or liquids capable in pure form of absorbing at least 95% of the ultraviolet radiation at wavelengths in the range from about 290 to 320 nm, the radiation primarily responsible for causing sunburn. The materials may transmit some or all UV radiation above 320 nm, particularly if tanning is desired. The presently known UV absorptive materials which are accepted as safe for human use may be classified into five groups, as set forth in Table 6.1.

TABLE 6.1

| Group | Exemplary Compounds | Absorbance |
|---|---|---|
| Aminobenzoates | p-Aminobenzoic acid (PABA) | 260–313 nm |
| | Ethyl 4-[bis(hydroxypropyl)] aminobenzoate | 280–330 nm |
| | Octyl dimethyl PABA | — |
| | PABA propoxylate | — |
| | Glyceral PABA | 264–315 nm |
| | 2-Ethylhexyl PABA (Padimate O) | — |
| | Pentyl PABA (Padimate A) | — |
| Cinnamates | Cinoxate | 270–328 nm |
| | Diethanolamine p-methoxy cinnamate | 280–310 nm |
| | 2-Ethylhexyl p-methoxycinnamate | 290–320 nm |
| Benzones | Dioxybenzone | 260–320 nm |
| | Sulisobenzone | — |
| | Oxybenzone | 270–350 nm |
| | 2-Ethylhexyl 2-cyano-3,3-diphenylacrylate | — |
| Salicylates | 2-Ethylhexyl salicylate | 280–320 nm |
| | Triethanol amine salicylate | 260–320 nm |
| | Homosalate | 295–315 nm |
| Miscellaneous | Red petrolatum | — |
| | Titanium dioxide | — |
| | Digalloyl trioleate | 270–320 nm |
| | Lawsone with dihydroxyacetone | 290–400 nm |
| | 2-Phenylbenzimidazole-5-sulfonic acid | 290–320 nm |

The UV absorptive substances listed in Table 6.1 may be alone or in mixtures of two or more when it is desired to increase the range of UV absorption over that offered by any one substance. When combining UV absorptive substances, care should be taken to avoid undesirable interactions between the substances.

Use of octyl dimethyl PABA as the UV absorptive substance is preferred. Surprisingly, it has been found that the polymerization reaction is promoted by the presence of octyl dimethyl PABA as the porogen (as discussed below). Polymerization time, which may be about 10 to 12 hours with most porogens, is reduced to about 5 to 6 in the presence of octyl dimethyl PABA.

The sunscreen composition of the present invention may be incorporated in a suitable carrier or into cosmetic preparations, such as face creams, lipsticks, lip balms, baby creams, lotions, shampoos, after shave lotions, hair grooming preparations, and the like. Alternatively, the sunscreen composition, which is a dry, free-flowing powder, may be utilized by itself without further incorporation in a carrier of any kind.

The polymeric beads prepared as just described function as a reservoir for controlled delivery of the retained UV absorptive substances providing a wide range of advantages over the conventional formulations. Release of the UV absorptive substances from the pores occurs in sustained manner, providing a continuous fresh supply of active substance to the epidermal area to which the preparation has been applied. The UV absorptive substances diffuse out of the pores into either the vehicle if one is used or the natural bodily secretions present on one's skin at the applied area, in accordance with known principles of the diffusion of one liquid through another. The activity-time curve of the UV absorptive substance is thus extended and flattened out. The magnitude of the release rate is controlled by the pore volume distribution in the bead itself, notably the total pore volume and the average pore diameter. Selection of the values of these parameters according to predetermined standard provides control of the release rate to desired levels.

The following examples are offered by way of illustration, not by way of limitation.

6.1 Example

A two-liter four-necked reaction flask equipped with a stirrer driven by a variable speed motor, reflux condenser, thermometer, and nitrogen-inlet tube was set up. A slow flow of nitrogen was maintained through the reaction flask at all times. An aqueous phase made up at 350 parts of deionized water, 1.8 parts of gum arabic, and 1.8 parts sodium lignosulfate (Marasperse N-22, available from Reed Lignin, Inc.) was added to the flask, and an organic solution made up 39.65 parts of styrene, 47.60 parts of commercial divinylbenzene (55.6% divinylbenzene, 42.3% ethylvinylbenzene), 71.35 parts of heptane, and 2.2 parts benzoyl peroxide (70% active ingredient and 30% water) was dispersed in the aqueous phase with rapid agitation (stirrer speed approximately 950 rpm) to obtain a plurality of droplets having an average droplet diameter of below about 60 microns as determined by visual observation of a sample of the droplets with an optical microscope.

The reaction mixture was then heated to about 75° C. and maintained at that temperature for 10 hours to form porous beads of cross-linked styrene/divinylbenzene copolymer having heptane entrapped within the pores. The reaction mixture was then cooled to room temperature and the resulting polymeric beads collected by filtration, washed three times with 1000 parts of deionized water, and three times with 1000 parts of acetone, then dried in a vacuum oven at 80° C. for 24 hours.

The calculated or theoretical cross-link density of the purified beads is 30.3%. This density is calculated by multiplying the weight of divinylbenzene (47.6 g) by the purity of the divinylbenzene (0.556) to get the actual weight of pure divinylbenzene which is then divided by the total weight of monomer (87.25 g).

The surface area of a sample of the purified beads was 146.2m$^2$/g as measured by B.E.T. nitrogen multipoint analysis and the pore volume was 0.99 ml/g as measured by mercury porosimetry.

6.2 Example

A two-liter-necked reaction flask equipped as described in Example 6.1 was evacuated and purged with nitrogen. An aqueous phase made up of 450 parts of deionized water, 4 parts of gum arabic, and 4 parts of sodium lignosulfate was added to the flask, and an organic solution made up 52 parts of methylmethacrylate, 78 parts ethyleneglycol dimethacrylate, 1.5 parts of benzoyl peroxide (70% in water), and 150 parts of toluene was dispersed in the aqueous phase with rapid (stirrer speed approximately 900 rpm) to obtain a plurality of droplets having an average droplet of below about 60 microns, as determined by visual observation of a sample of the droplets being stabilized by the dispersants.

The reaction mixture was heated to 65° C. for 1 hour, then 75° C. and allowed to remain at this temperature for approximately 7 hours while maintaining a nitrogen flow of 2 ml/minute to form porous beads of cross-linked methacrylate/ethyleneglycoldimethacrylate copolymer having toluene entrapped within the pores. The reaction mixture was then cooled and the beads collected by filtration, washed three times with 1000 parts of deionized water, and three times with 1000 parts of acetone, then dried in a vacuum oven at 80° C. for about 24 hours.

The calculation of theoretical cross-link density of the purified beads is 60% and is calculated by dividing the weight of ethyleneglycoldimethacrylate (78 g) by the weight of monomer (130 g).

The surface area of a sample was 180.59 $m^2/g$ and the pore volume was 0.684 ml/g, determined as described in Example I above.

6.3 Example

A 25 parts portion of macroporous cross-linked copolymer beads as described in Example 6.1 above was mixed at room temperature with 100 parts of isopropanol in a glass beaker with a stirring bar. Then 25 parts of octyl dimethyl PABA were added slowly with stirring. The solvent was then allowed to evaporate to dryness in a fume hood at room temperature. The beads containing 49.7% octyl dimethyl PABA entrapped within their pores are obtained.

6.4 Example

By repeating the procedure of Example 6.3, using 25 parts of the styrene/divinylbenzene porous cross-linked polymeric beads prepared in Example I, 25 parts of 2-ethylhexyl-p-methoxycinnate and 100 parts of isopropanol as the solvent, beads containing 49.0% 2-ethylhexyl-p-methoxycinnanamate entrapped within their pores are obtained.

6.5 Example

By again repeating the procedure of Example 6.4 using 50 parts of the methylmethacrylate/ethyleneglycoldimethacrylate polymeric beads prepared by Example 6.2, 50 parts of a mixture of octyldimethyl PABA and oxybenzone-3 (7 parts of octyldimethyl PABA and 3 parts of oxybenzone-3), and 140 parts of isopropanol as the solvent, beads containing 49.6% octyldimethyl PABA/oxybenzone-3, entrapped within their pores are obtained.

6.6 Example

A two-liter four-necked reaction flask equipped with a stirrer driven by a variable speed motor, reflux condenser, thermometer, and nitogen inlet tube was set up. A slow flow of nitrogen was maintained through the reaction flask, and an aqueous phase consisting of 4.5 g gum arabic and 4.5 g sodium lignosulfate (Marasperse N-22, available from Reed Lignin, Inc.) was added to 450 ml of deionized water in the flask. An organic solution made up of 52.0 g methyl methacrylate glycol dimethacrylate and 78.0 g ethylene glycol dimethacrylate is stirred in a separate beaker, and 150.0 g of octyl dimethyl PABA added thereto. The organic solution with octyl dimethyl PABA was then added to the reaction flask without stirring, and 2.0 g benzoyl peroxide dissolved in 20.0 g methyl methacrylate in a separate beaker. The benzoyl peroxide-methacrylate solution was then poured into the flask while continuing to purge with a slow stream of nitrogen. After addition of the benzoyl peroxide methyl methacrylate solution, the mixture was stirred at 2600 rpm for about 10 minutes. Sample of the monomer droplets were obtained and examined, and the stirring speed adjusted to obtain an average droplet size of about 45 microns. The stirring speed was reduced to 1300 rpm after the desired particle size had been obtained. The reaction mixture was then heated to 40° C. and maintained at that temperature for 30 minutes, and the temperature then increased to 60° C. for 5.5 hours. After cooling the mixture to room temperature, the polymer beads were collected on a Buchner funnel under vacuum, washed three times with one liter of water, and dried under a fume hood.

The calculated cross-linking density of the polymer beads was 52%. The surface area of the beads was 59.4 $m^2/g$ and the pore volume was 0.37 cc/g.

An organic extraction using isopropanol was performed on the polymeric beads containing octyldimethyl PABA. The solvent was then evaporated and the compound obtained was analyzed by infrared and nuclear magnetic spectroscopy, as well as elemental analysis. The spectra and the results of the elemental analysis indicated that compound had the expected structure of octyl dimethyl PABA. Thus, the one-step preparation process did not degrade the octyl dimethyl PABA in any significant manner.

7 Vitamins and Vitamin Derivatives

Any vitamin, vitamin derivative or vitamincontaining substance which can be applied topically to human or animal skin can be absorbed in the above-described minute polymer beads to form the novel, macroporous, high capacity topical delivery systems of this invention. The chemical nature of each species will establish whether or not it can be used in the one step procedure. Retinoids, for example, will in general only be used in the two step procedure. Vitamin E acetate and lineoleate, on the other hand, can be used in the one step procedure.

7.1 Example

A 2000 ml four-necked reaction flask equipped with a motorized stirrer, reflux condenser, thermometer, and nitrogen inlet was evacuated and purged with nitrogen. 800 parts of deionized water, 6.4 parts of gum arabic and 6.4 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture was then added a freshly prepared solution of 90.5 parts of styrene (99.8% purity), 55 parts of commercial divinylbenzene (55.6% divinyl benzene, 42.3% ethylvinylbenzene), 2 parts benzoyl peroxide (70% active ingredient and 30% water), and 69.4 parts of heptane (porogen). The aqueous phase and organic solution were agitated by stirring at a rate adjusted to give a plurality of droplets having an average droplet diameter of about 10–60 microns, as determined by visual observation of a sample of the droplets with an optical microscope (400X) with the droplets being stabilized by the dispersants. This rate was approximately 1200 rpm. The reaction mixture was then heated to about 80° C. and maintained at that temperature for about 12 hours, at the previously adjusted stirring rate, to form porous beads of cross-linked styrene/divinylbenzene copolymer having toluene entrapped within the network of pores. The mixture was then cooled and the porous polymeric beads are removed from the reaction flask by filtration. The filtered beads were washed initially three times with one liter portions of deionized water to remove the dispersants, followed by three washes with 0.6 liter portions of isopropanol to remove any residual, unreacted monomer and the toluene used as the porogen during polymerization. The beads were then dried in an oven at 80° C. for eight hours.

The average particle diameter of these beads, which are white and opaque in appearance, indicating their macroporosity, was less than 35 microns, as measured by a mercury intrusion porosimeter or by optical microscopy.

The calculated or theoretical cross-linking density of the purified beads was 21.01%. This density was calculated by multiplying the weight of divinylbenzene (55 parts) by the purity of the divinylbenzene (0.556) to get the actual weight of pure divinylbenzene which was then divided by the total weight of monomer (90.5 parts + 55 parts) and multiplied by 100.

The surface area of a sample of the purified beads was determined by the B.E.T. method to be 36.41 meters$^2$/gram while the pore volume was determined by nitrogen adsorption isotherm to be 0.206 ml/gram. The B.E.T. method is described in detail in Brunauer, S. Emmet, P. H., and Teller, E., *J. Am. Chem. Soc.*, 60, 309–16 (1938). The nitrogen adsorption isotherm method is described in detail in Barrett, E. P., Joyner, L. G. and Helenda, P. P., *J. Am. Chem. Soc.*, 73, 373–80 (1951).

7.2 Example

The procedure of Example 7.1 was repeated in every essential detail, except for the following: 800 parts of deionized water were used to dissolve 5.6 parts of gum arabic and 5.6 parts of Marasperse N-22 at about 23° C.; 105 parts of styrene and 9.5 parts of divinylbenzene were used; 2.8 parts of benzoyl peroxide (70% active ingredient and 30% water) and 120 parts of heptane were employed during polymerization and stirring was adjusted to give an average droplet diameter of below about 50 microns (rate approximately 800–1600 rpm); three 300 ml portions of isopropanol were used to wash the beads. The macroporous cross-linked polymer beads obtained had the following characteristics:

| | |
|---|---|
| Calculated Cross-linking Density, %: | 26.4 |
| Average Particle Diameter, μ: | 25 |
| Surface Area, m$^2$/g: | 85.9 |
| Pore Volume, ml/g: | 0.44 |

7.3 Example

A two liter four-necked reaction flask equipped as described in Example 7.1 was evacuated and purged with nitrogen. An aqueous phase made up of 600 parts of deionized water, 6.0 parts of gum arabic and 6.0 parts of Marasperse N-22 was added to the flask, and an organic solution made up of 72.0 parts of methyl methacrylate, 78.0 parts of ethylene glycol dimethacrylate, 2.0 parts of benzoyl peroxide (70% active ingredient and 30% water) and 108.4 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets with an optical microscope (400 ×), with the droplets being stabilized by the dispersants.

The reaction mixture was then heated to 80° C. and maintained at that temperature for 12 hours while maintaining a nitrogen flow of 6 ml/minute, to form porous beads of cross-linked methyl methacrylate/ethylene glycol dimethacrylate copolymer having toluene entrapped within the pores. The reaction mixture was then cooled and the beads were collected by filtration, washed three times with 1000 part portions of water, then three times with 1000 part portions of isopropanol, and then dried at 80° C. for about 8 hours.

The calculated or theoretical cross-linking density of the purified beads was 52%, and was calculated by dividing the weight of ethylene glycol dimethacrylate (78.0 parts) by the total weight of monomer (72.0 parts + 78.0 parts) and then multiplying by 100.

The surface area of a sample of the purified beads is 96 meters$^2$/gram and the pore volume is 0.36 ml/gram, determined as described in Example 7.1 above.

7.4 Example

The procedure of Example 7.3 was again repeated in every essential detail except for the following: 400 parts of deionized water were used to dissolve 4.0 parts of gum arabic and 4.0 parts of Marasperse N-22; 70 parts of methyl methacrylate and 30 parts of ethylene glycol dimethacrylate were used; 1.0 part of lauroyl peroxide and 69.4 parts of toluene were employed during polymerization; the reaction was conducted at 85° C. for 12 hours. The resulting polymer beads were collected and washed with three 1000 ml portions of deionized water followed by three 1000 ml portions of isopropanol, and then dried at 80° C. for about 8 hours. The macroporous cross-linked polymer beads obtained had the following characteristics:

| | |
|---|---|
| Calculated Cross-linking Density, %: | 30 |
| Average Particle Diamter, μm: | 30 |
| Surface Area, M$^2$/g: | 12.54 |
| Pore Volume, ml/g: | 0.170 |

7.5–7.7 Examples

By repeating the procedure of Example 7.4 in every essential detail except for the weights of monomers and solvents employed, the macroporous cross-linked polymer beads described in Table 7.1 below were obtained.

TABLE 7.1

| Example | Methyl Methacrylate, g | Ethylene Glycol Dimethacrylate, g | Porogen Toluene, g | Cross-linking Density, % | Calculated Particle Diameter, um | Average Surface Area m$^2$/g | Pore Volume, ml/g |
|---|---|---|---|---|---|---|---|
| 5 | 20.0 | 80.0 | 85.6 | 80.0 | 30 | 301.93 | 0.553 |
| 6 | 40.0 | 60.0 | 69.4 | 60.0 | 25 | 95.07 | 0.368 |
| 7 | 80.0 | 20.0 | 86.7 | 20.0 | 40 | 0.72 | 0.044 |

7.8 Example

A 70 part portion of the macroporous cross-linked polymer beads prepared as described in Example 7.3 above was mixed at room temperature with 157 parts of isopropanol in a glass beaker with an agitator. 30 parts of vitamin E linoleate are added slowly, with stirring, and the resulting suspension is stirred for about five minutes. The solvent is then allowed to evaporate to dryness in a fume hood at room temperature for 2 days. The beads contain 30.0% vitamin E linoleate entrapped within their macropores.

7.9 Example

By repeating the procedure of Example 7.8 using 35 parts of the styrene divinylbenzene macroporous cross-linked polymer beads prepared as described in Example 7.2, 15 parts of vitamin E linoleate and 86.7 parts of isopropanol as the solvent, beads containing 30% vitamin E linoleate entrapped within their macropores are obtained.

7.10 Example

By again repeating the procedure of Example 7.8 using 350 parts of the methyl methacrylate/ethylene glycol dimethacrylate macroporous cross-linked polymer beads prepared as described in Example 7.3, 160 parts of vitamin E linoleate and 200 parts of isopropanol, beads containing 32% vitamin E linoleate entrapped within their macropores are obtained.

7.11-7.16 Examples

The procedure of Example 7.8 is repeated using the following vitamins, vitamin derivatives, vitamin-containing substances and solvents in the indicated amounts:

| Active Ingredient, parts | Macroporous Polymer, parts | Solvent, parts |
|---|---|---|
| Vitamin A, 1.0 | 1.0 | Ethanol, 4.0 |
| Vitamin D, 30.0 | 30.0 | Isopropanol, 39.0 |
| Vitamin E, 30.0 | 30.0 | Isopropanol, 39.0 |
| Vitamin E. Acetate, 35.0 | 15.0 | Ethanol, 78.5 |
| Vitamin E Palmitate, 35.0 | 15.0 | Ethanol, 78.5 |
| Cod Liver Oil, 40.0 | 40.0 | Isopropanol, 125.6 |

In each case, methyl methacrylate/ethylene glycol dimethacrylate macroporous cross-linked polymer beads containing the respective active ingredients in the following percentages are obtained.

| Active Ingredient | % |
|---|---|
| Vitamin A | 50 |
| Vitamin D | 50 |
| Vitamin E | 50 |
| Vitamin E acetate | 30 |
| Vitamin E palmitate | 30 |
| Cod liver oil | 50 |

7.17 Example

Three 0.4 gram portions of each of:
1. commercially available night cream;
2. the same commercially available night cream admixed with 1% vitamin E linoleate; and
3. the same commercially available night cream admixed with 1% polymer beads containing entrapped vitamin E linoleate (entrapped vitamin E linoleate equals 32% of the weight of beads), are rubbed onto three separate areas on a volunteer's lower arm. The viscoelastic properties of the treated skin of the arm were measured over a five minute period with an electrodynamometer. The technique is described in detail in M. S. Christensen, C. W. Hargens III, S. Nacht, and E. H. Gans, *J. Invest. Dermatol,* 69 282 (1977).

The three areas are rubbed, applying equal pressure to each, after 15 and 24 hours. The results of the tests, in terms of percent increase in skin softening and release upon demand of the substances tested are measured.

The first compound is the commercially available night cream. It exhibits between a 25% and 30% increase in skin softening about one hour after application, increasing to about 40% skin softening approximately five hours after the initial application. Over the next 10 hours, its effectiveness rapidly declines to a 0% increase in skin softening. Rubbing the area to which the night cream was applied 15 hours after application has no effect.

The second compound is the night cream with admixed 1% vitamin E linoleate. It exhibits about a 40% increase in skin softening one hour after application, increasing to around 44% at five hours after application. It then drops to about a 15% increase over the next 10 hour period. Fifteen hours after application, the affected area is rubbed, causing the % increase in skin softening to remain level at 15% for nearly an hour before dropping to zero an hour later.

The third compound is the night cream with admixed 1% polymer beads that contain vitamin E linoleate, where the entrapped vitamin E linoleate is 32% of the weight of the beads. One hour after application, this compound exhibits between a 30% and 35% increase in skin softening. This increases to approximately 44% at the five hour mark. Over the next ten hours, this value declines to zero. By rubbing the skin area fifteen hours after the initial application, the increase in skin softening rapidly increases to between 20 and 25% over the next hour before declining to zero. Thus, a release of the active ingredient from the polymer beads can be effected at will be simply rubbing the area to which the beads were applied, even many hours after the initial application.

7.18 Example

A 2000 ml four-necked reaction flask equipped with a motorized stirrer, reflux condenser, thermometer, and nitrogen inlet was evacuated and purged with nitrogen. 1200 parts of deionized water, 9.6 parts of gum arabic and 9.6 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 90.5 parts of styrene (99.8% purity), 55 parts of commercial divinylbenzene (55.6% divinyl benzene, 42.3% ethylvinylbenzene), 2 parts of benzoyl peroxide (70% active ingredient and 30% water), and 69.4 parts of heptane. The aqueous phase and organic solution were agitated by stirring at a rate adjusted to give a plurality of droplets having an average droplet diameter of about 10-60 microns, as determined by visual observation of a sample of the droplets with an optical microscope (400X) with the droplets being stabilized by the dispersants. This rate is approximately 1200 rpm. The reaction mixture was then heated to about 85° C. and maintained at that temperature for about 12 hours, at the previously adjusted stirring rate, to form porous beads of cross-linked styrene/divinylbenzene copolymer having heptane entrapped within the network of pores. The mixture was then cooled and the porous polymeric beads were removed from the reaction flask by filtration. The filtered beads were washed initially three times with one liter portions of deionized water to remove the dispersants, followed by three washes with one-liter portions of isopropanol to remove any residual, unreacted monomer and porogen. The beads were then dried in an oven at 80° C. for eight hours. The average particle diameter of these beads, which were white and opaque in appearance, indicating their macroporosity, was less than 35 microns, as measured by a Sedimentation Micromeritics Microsizer 5300, an instrument available from Micromeritics Instrument Company, Norcross, Ga. The particle diameter determination method is described in detail in the "Microsizer 5300 Particle Size Analyzer Instruction Manual" (1984) associated with the instrument.

The calculated or theoretical cross-linking density of the purified beads is 21.01%. This density is calculated by multiplying the weight of divinylbenzene (55 parts) by the purity of the divinylbenzene (55.6%) to get the actual weight of pure divinylbenzene which is then divided by the total weight of monomer (90.5 parts +55 parts) and multiplied by 100.

The surface area of a sample of the purified beads was determined by the B.E.T. nitrogen multipoint analysis to be 36.41 m$^2$/g while the pore volume was determined by the mercury intrusion method to be 0.206 cc/g. The B.E.T. method is described in detail in Brunauer, S., Emmet, P. H., and Teller, E., *J. Am. Chem. Soc.*, 60, 309-16 (1938). The mercury intrusion method is described in detail in "Advanced Experimental Techniques in Powder Metallurgy," pages 225-252, (Plenum Press, 1970).

7.19 Example

The procedure of Example 7.18 was repeated in every essential detail, except for the following: 750 parts of deionized water were used to dissolve 7.0 parts of gum arabic and 7.0 parts of Marasperse N-22 at about 23° C.; 75 grams of styrene and 75 grams of divinylbenzene were used; 1.0 part of benzoyl peroxide and 65.03 parts of heptane were employed during polymerization and stirring was adjusted to give an average droplet diameter of below about 50 microns (rate approximately 800-1600 rpm); and three 300-ml portions of isopropanol were used to wash the beads. The macroporous cross-linked polymer beads obtained had the following characteristics:

| | |
|---|---|
| Calculated Cross-linking Density, %: | 27.8 |
| Average Particle Diameter, microns: | 25 |
| Surface Area, m$^2$/g: | 59.43 |
| Pore Volume, cc/g: | 0.377 |

7.20 Example

A two-liter four-necked reaction flask equipped as described in Example 1 was evacuated and purged with nitrogen. An aqueous phase made up of 600 parts of deionized water, 6.0 parts of gum arabic and 6.0 parts of Marasperse N-22 was added to the flask, and an organic solution made up of 72.0 parts of methyl methacrylate, 78.0 parts of ethylene glycol dimethacrylate, 2.0 parts of a 70% aqueous solution of benzoyl peroxide and 108.4 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets with an optical microscope (400X), the droplets being stabilized by the dispersants.

The reaction mixture was then heated to 85° C. and maintained at that temperature for 12 hours while maintaining a nitrogen flow of 2 ml/minute, to form porous beads of cross-linked methyl methacrylate/ethylene glycol dimethacrylate copolymer having toluene entrapped within the pores. The reaction mixture was then cooled and the beads collected by filtration, washed three times with 1000 part portions of water, and three times with 1000 part portions of isopropanol, then dried in air at 80° C. for about 8 hours.

The calculated or theoretical cross-linking density of the purified beads is 52%, and was calculated by dividing the weight of ethylene glycol dimethacrylate (78.0 parts) by the total weight of monomer (150 parts), and then multiplying by 100.

The surface area of a sample of the purified beads is 96 m$^2$/g and the pore volume is 0.36 cc/g, determined as described in Example 1 above.

7.21-7.22 Examples

By repeating the procedure of Example 7.20 in every essential detail except for the weights of monomers employed, the macroporous cross-linked polymer beads described in the following table were obtained.

| | Example 4 | Example 5 |
|---|---|---|
| Methyl Methacrylate, g | 48.0 | 40.0 |
| Ethylene Glycol Dimethacrylate, g | 52.0 | 60.0 |
| Calculated Cross-linking Density, % | 51.0 | 58.8 |
| Average Particle Diameter, microns | 30 | 25 |
| Surface Area, m$^2$/g | 92.70 | 95.07 |
| Pore Volume, cc/g | 0.366 | 0.368 |

7.23 Example

A 6-part portion of the macroporous cross-linked polymer beads prepared in Example 7.18 above is mixed at room temperature with 4 parts of retinoic acid (all-trans-form) dissolved in 10 ml of ethanol. The resulting suspension is hand-stirred for a few minutes, and the solvent in then allowed to evaporate to dryness in a fume hood at room temperature. The beads are calculated to contain 40% of retinoic acid retained within the pores.

7.24 Example

A 10-part portion of the macroporous cross-linked polymer beads prepared in each of Examples 7.19 through 7.22 is mixed at room temperature with 4 parts of retinoic acid (all-trans-form) dissolved in a solution of 8 parts of isopropyl myristate and 8 parts of isopropanol. The resulting suspension is hand-stirred and the solvent is then allowed to evaporate. The beads are calculated to contain 18.2% of retinoic acid and 36.4% of isopropyl myristate retained within the pores.

8 Counterirritants

Counterirritants which may be utilized in accordance with the present invention include any of the wide variety of substances known to have counterirritant properties. This extends to both liquids and solids, the solids being dissolved in a suitable solvent to form liquid solutions prior to their use in the present invention. While these substances vary widely in chemical and physical nature, some of the best known examples are as follows: camphor and its homologues, menthol and its homologues, thymol and its homologues, and like substances, e.g. other terpenes and terpene-like materials, such as turpentine oil and pine oil, salicylate esters, e.g., methyl salicylate, triethanolamine salicylate and glycol salicylates, salicylamide, allyl isothiocyanate, chloral hydrate, methyl nicotinate, o-tocopheryl nicotinate, eucalyptus oil, capsicum preparations (capsaicin, capsicum and capsicum oleoresin), clove oil, histamine dihydrochloride and other substances which contain these materials, e.g., oil of wintergreen (containing methyl salicylate), peppermint oil (containing menthol), mustard oil (containing allyl isothiocyanate), and the like. Counterirritants are also used in the following mixtures:

camphor and menthol;
menthol and methyl salicylate;
menthol and thymol;
methyl nicotinate and methyl salicylate;
turpentine and camphor;
menthol, methyl salicylate and thymol;
methyl salicylate, menthol and methyl nicotinate;
methyl salicylate, camphor and menthol;
menthol, methyl salicylate and eucalyptus oil;
menthol, methyl salicylate and capsicum oleoresin;
methyl nicotinate, capsicum oleoresin and dipropylene glycol salicylate;
methyl salicylate, methyl nicotinate and capsicum oleoresin;
camphor, menthol, methyl salicylate and capsicum;
methyl salicylate, clove oil, menthol and eucalyptus oil;
methyl salicylate, menthol, eucalyptus oil and turpentine oil,
methyl salicylate, menthol, camphor and methyl nicotinate;
methyl salicylate, thymol, eucalyptus oil and menthjol;
methyl salicylate, menthol, camphor, eucalyptus oil and mustard oil;
methyl salicylate, menthol, camphor, monoglycol salicylate and methyl nicotinate;
methyl salicylate, capsicum, camphor, menthol and methyl nicotinate;
camphor, methol, methyl salicylate, mustard oil and glycol monosalicylate; and
turpentine oil, pine oil, camphor, methyl salicylate and capsicum oleoresin.

Counterirritants of particular interest in the present invention are menthol, camphor and methyl salicylate.

Examples of organic solvents in which such substances can be dissolved to facilitate absorption include liquid petrolatum, petroleum ether, ethanol (especially for menthol and thymol) higher alcohols (especially for camphor), isopropyl myristate, diisopropyl adipate, and mineral oil. The solvent can then be evaporated or, if desired, retained together with the absorbed substance within the pores. Other formulating materials, such as carriers or adjuvants and the like can also be present, and will be incorporated into and onto the beads together with the counterirritants and any other materials present.

8.1 Example

A 2000 ml four-necked reaction flask equipped with a motorized stirrer, reflux condenser, thermometer, and nitrogen inlet was evacuated and purged with nitrogen. 800 parts of deionized water, 6.4 parts of gum arabic and 6.4 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 102.3 parts of styrene (99.8% purity), 85.6 parts of commercial divinylbenzene (55.6% divinyl benzene, 42.3% ethylvinylbenzene), 5.3 parts of benzoyl peroxide (70% active ingredient and 30% water), and 130 parts of heptane. The aqueous phase and organic solution were agitated by stirring at a rate adjusted to give a plurality of droplets having average droplet diameter of about 10–60 microns, as determined by visual observation of a sample of the droplets with an optical microscope (400X) with the droplets being stabilized by the dispersants. This rate is approximately 1200 rpm. The reaction mixture was then heated to about 80° C. and maintained at that temperature for about 20 hours, at the previously adjusted stirring rate, to form porous beads of cross-linked styrene/divinylbenzene copolymer having heptane entrapped within the network of pores. The mixture was then cooled, diluted with 200 parts of water, and the porous polymeric beads were removed from the reaction flask by filtration. The filtered beads were washed initially three times with one liter portions of deionized water to remove the dispersants, followed by three washes with 0.6 liter portions of isopropanol: acetone mixture (7:3, respectively, by weight) to remove any residual, unreacted monomer and the heptane used as the porogen during polymerization. The beads were then dried in an oven at 80°–100° C. for eight hours. The average particle diameter of these beads was 25 microns, as measured by a Sedimentation Micromeritics Microsizer 5300, an instrument available from Micromeritics Instrument Company, Norcross, Ga. The particle diameter determination method is described in detail in the "Microsizer 5300 Particle Size Analyzer Instruction Manual" (1984) associated with the instrument.

The calculated or theoretical cross-linking density of the purified beads is 25%. This density is calculated by multiplying the weight of divinylbenzene (85.6 parts) by the purity of the divinylbenzene (55.6%) to get the actual weight of pure divinylbenzene which is then divided by the total weight of monomer (85.6 parts +102.3 parts) and multiplied by 100.

The surface area of a sample of the purified beads was determined by the B.E.T. nitrogen multipoint analysis to be 91.2 $m^2/g$ while the pore volume was determined by the mercury intrusion method to be 1.0 cc/g. The B.E.T. method is described in detail in Brunauer, S., Emmet, P. H., and Teller, E., *J. Am. Chem. Soc.*, 60, 309–16 (1938). The mercury intrusion method is described in detail in "Advanced Experimental Techniques in Powder Metallurgy," pages 225–252, (Plenum Press, 1970).

8.2–8.3 Examples

By repeating the procedure of Example 8.1 in every essential detail, except for the weights of monomers and porogen employed, porous cross-linked polymer beads were obtained having the following characteristics listed in Table 8.1:

TABLE 8.1

| | PORE CHARACTERISTICS OF DRY BEADS FROM STYRENE/DIVINYLBENZENE | | | | |
|---|---|---|---|---|---|
| Example | Porogen | Proportions: Styrene/Divinyl- Benzene/Porogen | Average Particle Diameter (microns) | Surface Area ($m^2/g$) | Pore Volume (cc/g) |
| 2 | Mineral Oil | 100/89/180 | 25 | 75 | 1.36 |
| 3 | Toluene | 85.6/102.3/188 | 25 | 1.8 | 0.04 |

8.4 Example

A two-liter four-necked reaction flask equipped as described in Example 8.1 was evacuated and purged with nitrogen. An aqueous phase made up of 800 parts of deionized water, 8 parts of gum arabic and 8 parts of Marasperse N-22 was added to the flask, and an organic solution made up of 100 parts of methyl methacrylate, 100 parts of ethylene glycol dimethacrylate, 10 parts of butyl methacrylate, 2 parts of lauroyl peroxide and 173 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets being stabilized by the dispersants.

The reaction mixture was then heated to 80° C. and maintained at that temperature for 6 hours while maintaining a nitrogen flow of 1 ml/minute, to form porous beads of cross-linked methyl methacrylate/butyl methacrylate/ethylene glycol dimethacrylate terpolymer having toluene entrapped within the pores. The reaction mixture was then cooled and the beads collected by filtration, washed three times with 1000 parts of water, and three times with 1000 parts of isopropanol, then dried in air at room temperature.

The calculated or theoretical cross-linking density of the purified beads is 47.6%, and was calculated by dividing the weight of ethylene glycol dimethacrylate (100 parts) by the total weight of monomer (210 parts), and then multiplying by 100.

The surface area of a sample of the purified beads is 52 $m^2/g$ and the pore volume is 0.4 cc/g, determined as described in Example 1 above.

8.5–8.8 Examples

By repeating the procedure of Example 8.4 in every essential detail except for the weights of monomers employed and, in one case, the porogen used, the porous cross-linked polymer beads described in Table 8.2 below were obtained.

TABLE 8.2

PORE CHARACTERISTICS OF DRY BEADS FROM METHYL METHACRYLATE (MMA) AND ETHYLENE GLYCOL DIMETHACRYLATE (EGDMA)

| Example | Porogen | Proportions: MMA/EGDMA/ Porogen | Average Particle Diameter (microns) | Surface Area ($m^2/g$) | Pore Volume (cc/g) |
|---|---|---|---|---|---|
| 5 | toluene | 100/100/173 | 25 | 73.8 | 0.405 |
| 6 | toluene | 150/150/450 | 15 | 95.8 | 0.508 |
| 7 | toluene | 100/100/200 | 25 | 84.0 | 0.38 |
| 8 | heptane | 210/90/200 | 15 | 2.34 | 0.58 |

8.9–8.15 Examples

In these examples, preformed dry polymer beads from Examples 8.1 through 8.5 were impregnated with counterirritants or counterirritant solutions at specified proportions by combining the beads and counterirritant (or its solution), then mixing the resulting wet powder until it was homogeneous. In all cases except Example 8.12, the beads and counterirritant were combined and mixed at room temperature. In Example 8.12, the menthol, which is solid at room temperature, was first melted to liquid form by heating to 80° C., which temperature was maintained as the compounds were combined and mixed Counterirritant contents of the finished products in all cases including Example 8.12 were then determined by extraction and analysis according to conventional techniques. The materials, proportions, and final counterirritant contents are listed in Table 8.3. Example 8.15 is a prophetic example.

TABLE 8.3

IMPREGNATED PARTICLES - PREPARATION AND ANALYSIS

| Example | Example From Which Beads Were Taken | Counterirritant Solution (Weight %) | Weight Ratio, Beads to Solution | Counterirritant Level in Product (Weight %) |
|---|---|---|---|---|
| 8.9 | 1 | 33% menthol in isopropyl myristate | 1:1 | 16.7 |
| 8.10 | 2 | 33% menthol in diisopropyl adipate | 1:1 | 16.7 |
| 8.11 | 3 | 41.7% menthol in mineral oil | 1:1 | 20.8 |
| 8.12 | 4 | 100% menthol | 3:2.45 | 44.8 |
| 8.13 | 5 | 50% menthol in ethanol | 1:1 | 25.0 |
| 8.14 | 1 | 30% camphor in isopropyl myristate | 6:4 | 12.0 |
| 8.15 | 1 | 100% methyl salicylate | 6:4 | 40.0 |

8.16 Example

A two-liter four-necked reaction flask equipped as described in Example 8.1 was evacuated and purged with nitrogen. An aqueous solution made of 800 parts of deionized water, 8 parts of gum arabic and 8 parts of Marasperse N-22 was added to the flask, and an organic solution made up of 120 parts of methyl methacrylate, 80 parts of ethylene glycol dimethacrylate, 10 parts of butyl methacrylate, 100 parts of menthol, 100 parts of mineral oil and 2 parts of lauroyl peroxide was dispersed in the aqueous phase were agitated by stirring at a rate adjusted to give a plurality of droplets having an average droplet diameter of about 10–60 microns. The reaction mixture was then heated to about 78° C. and maintained at that temperature for about 20 hours, to form porous beads of cross-linked methyl methacrylate/butyl methacrylate/ethylene glycol dimethacrylate terpolymer having mineral oil and menthol entrapped within the pores. The mixture was then cooled, diluted with 200 parts of water, and the porous polymeric beads were removed from the reaction flask by filtration. The filtered beads were washed three times with one liter portions of deionized water to remove the dispersants. The beads were then dried in air at room temperature.

The calculated or theoretical cross-linking density of the resulting polymeric beads was 38%, and was calculated by dividing the weight of ethylene glycol dimethacrylate (80 parts) by the total weight of monomer (210 parts), and then multiplying by 100.

The surface area of a sample of the purified beads was 1.076 m$^2$/g and the pore volume was 0.869 cc/g, determined as described in Example 1 above.

9 Epidermal Lipid Replacement Substances

Squalane, and in certain systems squalene as well, may be used as the porogen in a one step procedure. With squalene, the steps must be performed under an inert atmosphere such as nitrogen. If a polymerization catalyst is used, it must be one which does not oxidize squalene. Azo catalysts are examples of such catalysts. Also, polymerization temperatures are best held within a moderate range. In the case of squalane, on the other hand, such restrictions are generally less restrictive or not required.

9.1 Example

A 2000 ml four-necked reaction flask equipped with a motorized stirrer, reflux condenser, thermometer, and nitrogen inlet was evacuated and purged with nitrogen. 800 parts of deionized water, 6.4 parts of gum arabic and 6.4 parts of a sodium-based lignosulfonate available from Reed Lignins, Inc., under the trademark Marasperse N-22, were charged to the reaction flask. The mixture was heated, with stirring, in an oil bath at about 50° C. until the dispersants (gum arabic and lignosulfate) dissolved to form an aqueous phase.

To this mixture there was then added a freshly prepared solution of 102.3 parts of styrene (99.8% purity), 85.6 parts of commercial divinylbenzene (55.6% divinyl benzene, 42.3% ethylvinylbenzene), 5.3 parts of benzoyl peroxide (70% active ingredient and 30% water), and 130 parts of heptane. The aqueous phase and organic solution were agitated by stirring at a rate adjusted to give a plurality of droplets having an average droplet diameter of about 10–60 microns, as determined by visual observation of a sample of the droplets with an optical microscope (400X) with the droplets being stabilized by the dispersants. This rate is approximately 1200 rpm. The reaction mixture was then heated to about 80° C. and maintained at that temperature for about 20 hours, at the previously adjusted stirring rate, to form porous beads of cross-linked styrene/divinylbenzene copolymer having heptane entrapped within the network of pores. The mixture was then cooled, diluted with 200 parts of water, and the porous polymeric beads were removed from the reaction flask by filtration. The filtered beads were washed initially three times with one liter portions of deionized water to remove the dispersants, followed by three washes with 0.6 liter portions of isopropanol:acetone mixture (7:3, respectively, by weight) to remove any residual, unreacted monomer and the heptane used as the porogen during polymerization. The beads were then dried in an oven at 80°–100° C. for eight hours. The average particle diameter of these beads was 25 microns, as measured by a Sedimentation Micromeritics Microsizer 5300, an instrument available from Micromeritics Instrument Company, Norcross, Ga. The particle diameter determination method is described in detail in the "Microsizer 5300 Particle Size Analyzer Instruction Manual" (1984) associated with the instrument.

The calculated or theoretical cross-linking density of the purified beads is 25%. This density is calculated by multiplying the weight of divinylbenzene (85.6 parts) by the purity of the divinylbenzene (55.6%) to get the actual weight of pure divinylbenzene which is then divided by the total weight of monomer (85.6 parts + 102.3 parts) and multiplied by 100.

The surface area of a sample of the purified beads was determined by the B.E.T. nitrogen multipoint analysis to be 91.2 m$^2$/g while the pore volume was determined by the mercury intrusion method to be 1.0 cc/g. The B.E.T. method is described in detail in Brunauer, S., Emmet, P. H., and Teller, E., *J. Am. Chem. Soc.*, 60, 309–16 (1938). The mercury intrusion method is described in detail in "Advanced Experimental Techniques in Powder Metallurgy," pages 225–252, (Plenum Press, 1970).

9.2 Example

A two-liter four-necked reaction flask equipped as described in Example 9.1 was evacuated and purged with nitrogen. An aqueous phase made up of 600 parts of deionized water, 6.0 parts of gum arabic and 6.0 parts of Marasperse N-22 was added to the flask, and an organic solution made up of 72.0 parts of methyl methacrylate, 78.0 parts of ethylene glycol dimethacrylate, 2.0 parts of benzoyl peroxide and 108.4 parts of toluene was dispersed in the aqueous phase with strong agitation (stirrer speed approximately 1000 rpm) to obtain a plurality of droplets having an average droplet diameter of below about 50 microns, as determined by visual observation of a sample of the droplets with an optical microscope (400X), the droplets being stabilized by the dispersants.

The reaction mixture was then heated to 85° C. and maintained at that temperature for 12 hours while maintaining a nitrogen flow of 2 ml/minute, to form porous beads of cross-linked methyl methacrylate/ethylene glycol dimethacrylate copolymer having toluene entrapped within the pores. The reaction mixture was then cooled and the beads collected by filtration, washed three times with 1000 parts of water, and three times with 1000 parts of isopropanol, then dried in air at 80° C. for about 8 hours.

The calculated or theoretical cross-linking density of the purified beads is 52%, and was calculated by dividing the weight of ethylene glycol dimethacrylate (78.0 parts) by the total weight of monomer (150 parts), and then multiplying by 100.

The surface area of a sample of the purified beads is 96 m$^2$/g and the pore volume is 0.36 cc/g, determined as described in Example 1 above.

9.3 Example

Ten-part portions of preformed dry polymer beads from Examples 9.1 and 9.2 were each mixed at room temperature with a ten-part portion of an 67% solution of squalane in hexane. The resulting suspensions were hand-stirred for a few minutes. The hexane was then allowed to evaporate from the resulting wet powders at room temperature. The resulting beads contained 40% squalane entrapped within their macropores.

9.4 Example

The procedure of Example 9.3 was repeated in every detail except for the following: two ten-part portions of the preformed beads prepared as described in each of Examples 9.1 and 9.2 were used, with one of the portions of the beads from each example being admixed with a ten-part portion of an 67% solution of squalene in hexane, and with the other two portions of beads being admixed with ten-part portions of an 67% solution of 50:50 mixture of squalene and squalane in hexane. In all four cases, the beads contained 40% of the absorbed, entrapped impregnant or impregnant mixture within their micropores.

9.5 Example

A two-liter four-necked reaction flask equipped as described in Example 9.1 was evacuated and purged with nitrogen. A mixture made up of 900 parts of deionized water, 7.2 parts of gum arabic, and 7.2 parts of Marasperse N-22 was charged to the flask. The mixture was heated with stirring in an oil bath at about 50° C. until the dispersants (the gum arabic and the lignosulfonate) dissolved, to form an aqueous phase.

To this mixture there was then added a freshly prepared solution of 71 parts styrene (99.8% purity), 84 parts of commercial divinylbenzene (55.6% divinylbenzene and 42.3% ethylvinylbenzene), 7.0 parts of benzoyl peroxide (70% active ingredient, 30% water) and 135 parts of squalane. The aqueous and organic phases were agitated by stirring at a rate adjusted to give a plurality of droplets having an average droplet diameter of about 10–60 microns, as determined by visual observation of a sample of the droplets with an optical microscope (100X), the droplets being stabilized by the dispersants. This rate was approximately 1200 rpm. The reaction mixture was then heated to about 89° C. and maintained at that temperature for about 20 hours, at the previously adjusted stirring rate, to form porous beads of cross-linked styrene/divinylbenzene copolymer having squalane retained within the network of pores.

The mixture was then cooled, diluted with 200 parts of water, and the porous polymeric beads were removed from the reaction flask by filtration. The filtered beads were washed three times with one-liter portions of deionized water to remove the dispersants. The beads were then dried in air at room temperature.

The calculated or theoretical cross-linking density of the resulting polymeric beads was 30%, and was calculated by multiplying the weight of divinylbenzene (84 parts) by the purity of the divinylbenzene (55.6%) to get the actual weight of pure divinylbenzene which was then divided by the total weight of monomer (155 parts) and multiplied by 100.

The surface area of a sample of the purified beads was 0.88 m$^2$/g and the pore volume was 1.15 cc/g, determined as described in Example 9.1 above. Analysis for squalane indicated that the squalane content of the finished product was 41.8% by weight.

The foregoing description is directed primarily to preferred embodiments and practices of the present invention. It will be readily apparent to those skilled in the art that further changes and modifications in the actual implementation of the concepts described herein can be made without departing from the spirit and scope of the invention as defined by the following claims.

What is claimed is:

1. A method for preparing a delivery system for an active substance, said method comprising:
   polymerizing monomers suspended in an immiscible phase in the presence of a porogen to form a plurality of rigid cross-linked polymer beads each defining a substantially non-collapsible internal pore network having residual porogen therein, wherein the beads have a cross-linking density in the range from 20% to 80% and the pore network is open to the exterior of the beads;
   extracting substantially all residual porogen from the internal pore network; and
   introducing the active substance into the internal pore network after the porogen has been substantially completely extracted, whereby the porogen and polymerization conditions may be selected to provide pore dimensions which result in desired release characteristics for an active substance from the beads.

2. A method as in claim 1, further comprising removing unbound organic species from the internal pore network by washing the beads in a solvent after the residual porogen has been extracted and drying the solvent prior to introducing the active substance.

3. A method as in claim 1, further comprising topically applying the beads onto skin after the active substance has been introduced.

4. A method as in claim 1, further comprising introducing the beads into a topical carrier after the active substance has been introduced in the internal pore network.

5. A method as in claim 1, wherein the beads have a diameter in the range of from about 10 microns to about 40 microns.

6. A method as in claim 1, wherein the monomers are selected and polymerized under conditions which result in rigid cross-linked polymer beads having a total pore volume in the range from about 0.01 cc/g to about 4.0 cc/g, a surface area in the range from about 1 m$^2$/g to about 500 m$^2$/g, and an average pore diameter in the range from about 0.001 microns to about 3.0 microns.

7. A method as in claim 6, wherein the pore volume is in the range from about 0.1 cc/g to about 2.0 cc/g, the surface area is in the range from about 20 m$^2$/g to about 200 m$^2$/g, and the average pore diameter is in the range from about 0.003 microns to about 1.0 microns.

8. A method as in claim 1, wherein the monomers are selected to produce a copolymer selected from the group consisting of styrene-divinylbenzene and methyl methacrylate-ethylene glycol dimethacrylate.

9. A method as in claim 1, wherein the active substance is heat or radiation labile.

10. A method as in claim 9, wherein the active substance is selected from the group consisting of ultraviolet absorbants, vitamins, insect repellents, steroids, acne treatments, counterirritants, vitamins, and hair growth promotants.

11. A method as in claim 10, wherein the active substance is an ultraviolet absorbent selected from the group consisting of aminobenzoates, cinnamates, benzones, and salicylates.

12. A method as in claim 10, wherein the active substance is a retinoid.

13. A method as in claim 10, wherein the active substance is an insect repellent selected from the group consisting of terpenoids, benzoquinones, aromatics, and synthetics.

14. A method as in claim 10, wherein the active substance is a steroid selected from the group consisting of fluocinolone, flulocinolone acetonide, triamcinolone acetonide, betamethasone valerate, timobesone acetate, hydrocortisone, hydrocortisone acetate, triamcinolone, prednisolone, prednisolone acetate, dexamethasone, beclomethasone dipropionate, betamethasone dirporpionate, betamethasone benzoate, clocortolone pivalate, halcinonide, flumethasone, pivalate, and desonide.

15. A method as in claim 10, wherein the active substance is an acne treatment selected from the group consisting of benzoylperoxide, salicylic acid, and resorcinol.

16. A method as in claim 10, wherein the active substance is a counterirritant selected from the group consisting of camphor, methanol, and methyl salicylate.

17. A method as in claim 10, wherein the active substance is a fragrance selected from the group consisting of flower oils, essential oils from plants, animal scents, and synthetic substances.

18. A method as in claim 10, wherein the active substance is minoxidil.

* * * * *

UNITED STATES PATENT AND TRADEMARK OFFICE
CERTIFICATE OF CORRECTION

PATENT NO. : 5,145,675
DATED : September 8, 1992
INVENTOR(S) : Richard Won

It is certified that error appears in the above-indentified patent and that said Letters Patent is hereby corrected as shown below:

Title page: "Inventor: Richard Won, Palo Alto, Calif." should be changed to read --Inventors: Richard Won, Palo Alto, CA; Martin Katz, Menlo Park, CA; Chung-Heng Cheng, San Jose, CA--

Signed and Sealed this

Twenty-third Day of March, 1999

Attest:

Q. TODD DICKINSON

*Attesting Officer*     *Acting Commissioner of Patents and Trademarks*